United States Patent [19]

Schmidt et al.

[11] Patent Number: 4,980,348
[45] Date of Patent: Dec. 25, 1990

[54] CARBACEPHEM ANTIBIOTICS

[75] Inventors: Gunter Schmidt; Wolfgang Hartwig; Wilfried Schröck; Rainer Endermann; Karl G. Metzger; Ingo Haller, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 305,317

[22] Filed: Feb. 1, 1989

[30] Foreign Application Priority Data

Feb. 3, 1988 [DE] Fed. Rep. of Germany ....... 3803169

[51] Int. Cl.$^5$ ................. C07D 471/04; A61K 31/435
[52] U.S. Cl. ..................................... 514/210; 540/205
[58] Field of Search ......................... 540/205; 514/210

[56] References Cited

U.S. PATENT DOCUMENTS

| | | | |
|---|---|---|---|
| 4,226,866 | 10/1980 | Christensen | 540/205 |
| 4,255,424 | 3/1981 | Hannah | 540/205 |
| 4,537,886 | 8/1985 | Taylor | 540/205 |
| 4,694,001 | 9/1987 | Hirata | 540/205 |
| 4,760,060 | 7/1988 | Mochida | 540/205 |

FOREIGN PATENT DOCUMENTS

| | | | |
|---|---|---|---|
| 14476 | 8/1980 | European Pat. Off. | 540/205 |
| 0197294 | 10/1986 | European Pat. Off. | |
| 0195947 | 10/1988 | European Pat. Off. | |

Primary Examiner—Mark L. Berch
Attorney, Agent, or Firm—Sprung Horn Kramer & Woods

[57] ABSTRACT

A heteroanellated phenylglycine-β-lactam antibiotic of the formula

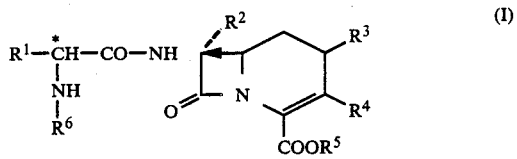

(I)

in which
$R^1$ - stands for a radical of the formula

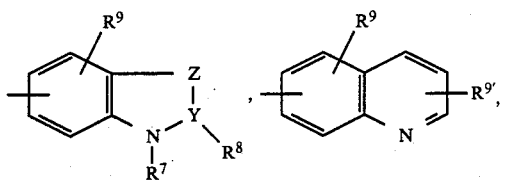

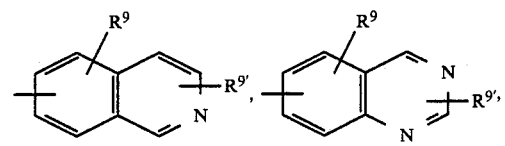

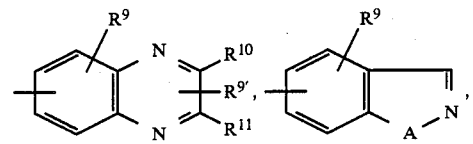

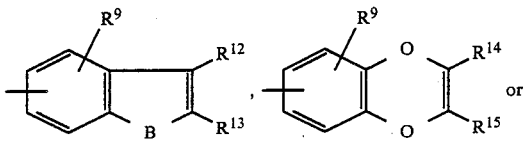

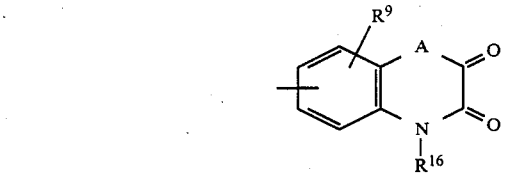

13 Claims, No Drawings

CARBACEPHEM ANTIBIOTICS

The invention relates to β-lactam antibiotics, processes for their preparation and their use as medicaments and in medicaments, in particular as antibacterial, orally active antibiotics.

It is known that various representatives of 7-α-aminoacylcephalosporins having different substituents in the 3-position of the molecule act as antibiotics, thus, for example, cephalexin [7-(D-α-phenyl-glycylamido)-3-methyl-3-cephem-4-carboxylic acid], cefaclor [7-(D-α-phenylglycylamido)-3-chloro-3-cephem-4-carboxylic acid] (compare GB Pat. No. 1,174,335; DE-OS (German Published Specification) No. 2,408,698 and DE-OS (German Published Specification) No. 2,728,578).

Furthermore, $C_3$-substituted cephalosporins are described as orally active compounds in DE-OS (German Published Specification) No. 3,508,258 and DE-OS (German Published Specification) No. 3,509,618.

The present invention relates to heteroanellated phenylglycine-β-lactam antibiotics of the general formula (I)

[Structure of formula (I): $R^1$—*CH—CO—NH— β-lactam ring with $R^2$, $R^3$, $R^4$, COOR$^5$, NH—$R^6$]

in which $R^1$ - stands for a radical of the formula

[Eight ring structures shown with substituents $R^9$, $R^{9'}$, $R^7$, $R^8$, $R^{10}$, $R^{11}$, $R^{12}$, $R^{13}$, $R^{14}$, $R^{15}$, $R^{16}$, Z, Y, A, B]

wherein

Y - stands for N or $CR^{17}$, or the grouping Y-$R^8$ - stands for $\rangle{=}O$ or $\rangle{=}N{-}R^8$, Z - stands for O, S or $-NR^{18}$,
A - stands for O, S or $-NR^{19}$,
B - stands for O or $-NR^{16}$,
$R^7$ - stands for hydrogen or
stands for hydroxyl or amino, or
stands for straight-chain, branched or cyclic alkyl or alkenyl having up to 10 carbon atoms, each of which is optionally substituted by halogen optionally substituted amino, hydroxyl, cyano or $C_6$-$C_{10}$-aryl, or
stands for optionally substituted $C_6$-$C_{10}$-aryl,
R8 - stands for hydrogen, or
stands for optically substituted $C_6$-$C_{10}$-aryl, or
stands for straight-chain, branched or cyclic alkyl or alkenyl having up to 10 carbon atoms, each of which is optionally substituted by halogen, hydroxyl, alkoxy or alkoxycarbonyl each having up to 6 carbon atoms, cyano, carbonyl, optionally substituted $C_6$-$C_{10}$-aryl, sulpho or by an optionally substituted amino group, or
$R^7$ and $R^8$ together complete a double bond,
$R^9$ and $R^{9'}$ are identical or different and
stand for hydrogen, or
stand for straight-chain, branched or cyclic alkyl, alkoxy or alkylthio each having up to 8 carbon atoms, or
stand for trifluoromethyl or trifluoromethoxy, or
stand for hydroxyl, mercapto, nitro, cyano or halogen, or
stand for an optionally substituted amino group,
$R^{10}$ and $R^{11}$ are identical or different and
stand for hydrogen, or
stand for optionally substituted $C_6$-$C_{10}$-aryl, or
stand for an optionally substituted amino group, or
stand for hydroxyl, or
stand for straight-chain, branched or cyclic alkoxy having up to 8 carbon atoms, or
stand for acyl or acyloxy each having up to 7 carbon atoms, or
stand for straight-chain, branched or cyclic, optionally substituted alkyl having up to 12 carbon atoms,
$R^{12}$ and $R^{13}$ are identical or different and
stand for hydrogen, or
stand for optionally substituted $C_6$-$C_{10}$-aryl, or
stand for heterocyclyl, or
stand for hydroxyl, or
stand for an optionally substituted amino group, or
for straight-chain, branched or cyclic alkoxy having up to 8 carbon atoms, or stand for acyl or acyloxy each having up to 7 carbon atoms, or stand for alkoxycarbonyl having up to 8 carbon atoms, or stand for optionally substituted straight-chain, branched or cyclic alkyl having up to 12 carbon atoms, or $R^{12}$ and $R^{13}$ together stand for the grouping of the formula

$R^{14}$ and $R^{15}$ are identical or different and stand for hydrogen, or stand for optionally substituted straight-chain, branched or cyclic alkyl having up to 12 carbon atoms, or stand for optionally substituted $C_6$–$C_{10}$-aryl, or stand for alkoxycarbonyl having up to 8 carbon atoms, $R^{16}$ stands for hydrogen, or for optionally substituted $C_6$–$C_{10}$-aryl, or stands for straight-chain, branched or cyclic alkyl having up to 8 carbon atoms, $R^{17}$ has the same meaning as $R^8$ and in addition stands for halogen, or for straight-chain, branched or cyclic alkoxy or alkylthio each having up to 8 carbon atoms, or stands for an optionally substituted amino group, stands for straight-chain, branched or cyclic alkylsulphonyl having up to 8 carbon atoms, or stands for phosphono, sulpho or sulphamoyl, or stands for mercapto, hydroxyl, phenylthio or phenoxy, or stands for guanidino, amidino, hydrazino or hydroxylamino, or stands for optionally substituted heterocyclyl, or stands for optionally substituted heterocyclyloxy or heterocyclylthio, $R^{18}$ has the same meaning as $R^{17}$, but does not complete a double bond with $R^8$, or $R^{17}$ and $R^{18}$ together stand for a $C_2$–$C_4$-methylene chain which is optionally interrupted by oxygen or sulphur and $R^{19}$ has the same meaning as $R^{15}$ and can be identical or different to this, $R^2$ - stands for hydrogen or methoxy, or for formamido, or for hydroxylamino, $R^3$ - stands for hydrogen, hydroxyl, alkyl or alkoxy having up to 6 carbon atoms, $R^4$ - denotes hydrogen, halogen, alkyl, alkoxy or alkylthio each having up to 4 carbon atoms, trifluoromethyl, methoxymethyl, vinyl, carbamoyloxymethyl or acetyloxymethyl, or stands for a group of the formula —CH=CH—CH₃, —CH=CH—C₂H₅, —CH=CH—CH₂Cl,

—CH=CH—CF₃, —CH=CH—CH₂OCH₃,

-continued

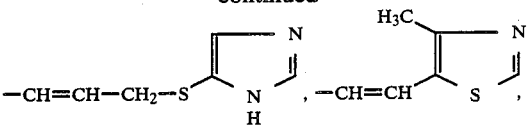

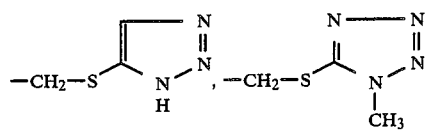

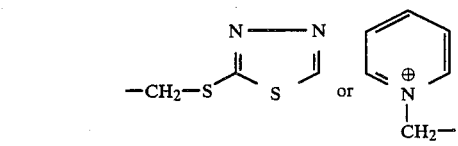

$R^5$ - stands for hydrogen, or for a carboxyl-protecting group, or for an ester radical which can be eliminated in vivo and $R^6$ - stands for hydrogen or for an amino-protecting group, and their pharmaceutically tolerable salts.

In the context of the abovementioned definition, aryl or aralkyl in general stands for a phenyl or benzyl radical, where the phenyl radicals can be monosubstituted to tetrasubstituted, preferably monosubstituted, disubstituted or trisubstituted, by identical or different substituents. Substituents which may be mentioned are: halogen, preferably fluorine, chlorine or bromine, straight-chain, branched or cyclic alkyl, alkoxy, alkylthio or alkylsulphonyl each having up to 10 carbon atoms, preferably up to 6 carbon atoms, halogenoalkyl, halogenoalkoxy or halogenoalkylthio each having up to 7 carbon atoms, preferably having up to 5 carbon atoms and having up to 5, preferably up to 3, chlorine and/or fluorine atoms, or nitro, cyano, benzyl, sulpho, amidino, sulphamoyl, carbamoyl or an optionally substituted amino group.

Optionally substituted alkyl in the context of the abovementioned definition in general stands for straight-chain, branched or cyclic alkyl preferably having up to 10 carbon atoms, suitable substituents being: halogen, alkoxy or alkylthio each having up to 8 carbon atoms, preferably having up to 6 carbon atoms, halogenoalkylthio or halogenoalkoxy each having up to 8 carbon atoms and up to 5, preferably up to 3, fluorine and/or chlorine atoms, nitro, cyano, an optionally substituted amino group, optionally substituted aryl, sulpho, sulphamoyl, alkylsulphonyl having up to 6 carbon atoms, preferably having up to 4 carbon atoms, hydroxyl, mercapto, acyloxy or acylthio each having up to 7 carbon atoms, carbamoyloxy, carboxyl, alkoxycarbonyl having up to 8 carbon atoms, preferably having up to 6 carbon atoms, phenoxy, phenylthio, benzyloxy or benzylthio.

Amino-protecting groups in the context of the abovementioned definition in general stand for a protecting group customary in β-lactam chemistry from the series comprising: benzyl, 2-nitrobenzyl, 4-nitrobenzyl, 4-methoxybenzyl, 2,4-dimethoxybenzyl, 3,4-dimethoxybenzyl, 2,4,6-trimethoxybenzyl, tert.-butoxycarbonyl, benzyloxycarbonyl, 2-nitrobenzyloxycarbonyl, 4-nitrobenzyloxycarbonyl, acetyl, chloroacetyl, trichloroacetyl, phenylacetyl, allyloxycarbonyl, 2,4-dimethoxybenzyloxycarbonyl, allyloxymethyl, bis-(4-methoxyphenyl)methyl, methoxymethyl, methylthiomethyl, methoxyethoxymethyl, 2-(methylthiomethoxy)ethoxycarbonyl, 2-hydroxy-2-phenylmethyl, methoxy-(4-methoxyphenyl)methyl, trimethylsilyl, triethylsilyl, triphenylsilyl, tert.-butyl-dimethylsilyl, tert.-butyl-diphenylsilyl, [2-(trimethylsilyl)ethoxy]methyl, 1-methyl-2-benzoyl-vinyl, 1-methyl-2-methoxyvinyl, 1-methyl-2-acetyl-vinyl, 1-methyl-2-(methoxybenzoyl)-vinyl, 1-methyl-2-(2,6-dimethoxybenzoyl)-vinyl and 1-methyl-2-ethoxycarbonyl-vinyl.

An optionally substituted amino group in general stands for the group

$R^{20}$ and $R^{21}$ are identical or different and
stand for hydrogen,
for aryl, preferably phenyl,
for $C_1$–$C_8$-alkyl, preferably $C_1$–$C_5$-alkyl,
for $C_7$–$C_{14}$-aralkyl, preferably benzyl or
for $C_2$–$C_{10}$-acyl, preferably acetyl or benzoyl.

The term heterocyclyl, heterocyclyloxy or heterocyclylthio in the context of the abovementioned meaning stands for saturated or unsaturated heterocycles, having up to 3 nitrogen atoms, an oxygen atom and/or a sulphur atom and optionally bonded via oxygen or sulphur, preferably for pyrrolyl, pyrrolidinyl, pyrazolyl, imidazolyl, pyridyl, pyridazinyl, pyrimidyl, pyrazinyl, quinolyl, isoquinolyl, indolyl, quinoxalyl, quinazonyl, piperidinyl, morpholinyl, piperazinyl, thiomorpholinyl, furyl, thienyl, oxazolyl, thiazolyl, isoxazolyl, thiadiazolyl, triazolyl or tetrazolyl.

If these heterocycles are substituted, then they are monosubstituted, disubstituted or trisubstituted, preferably monosubstituted or disubstituted, by identical or different straight-chain or branched alkyl, alkylthio or alkoxy each having up to 4 carbon atoms, preferably having 1 or 2 carbon atoms, halogen, preferably fluorine, chlorine or bromine, nitro, cyano, hydroxyl, amino, trifluoromethyl, trifluoromethoxy or trifluoromethylthio.

Carboxyl-protecting groups in the context of the abovementioned definition stand for the carboxyl-protecting groups customary in β-lactam chemistry. Groups which are easily eliminated are to be mentioned as preferred, such as, for example: methyl, ethyl, tert.-butyl, decyl, 2-chloroethyl, 2,2,2-trichloroethyl, cyanoethyl, diphenylmethyl, triphenylmethyl, acetoxymethyl, allyl, benzyl, 4-methoxyhenyl, 4-nitrobenzyl, 2-nitrobenzyl, 4-methoxybenzyl, 2,4-dimethoxybenzyl, trimethylsilylethyl, trimethylsilyl, tert.-butyl-dimethylsilyl, acetonyl, 1-phenoxyethyl and 2-methyl-2-propenyl.

If $R^5$ stands for an ester radical which can easily be eliminated in vivo, then pharmaceutically tolerable ester radicals are meant thereby, which are easily hydrolyzed in vivo to give free carboxyl groups ($R^5$=H).

Such ester radicals are well known in the β-lactam area. In most cases, they improve the absorption properties of the β-lactam compounds. In addition, the radical $R^5$ should be of such a type that it imparts pharmaceutically acceptable properties to a compound of the formula (I) and, on elimination, releases pharmaceutically acceptable fragments in vivo. Examples of such groups are found in DE-OS (German Published Specification) No. 2,517,316. Preferred ester groups which can be eliminated in vivo are those of the following formulae:

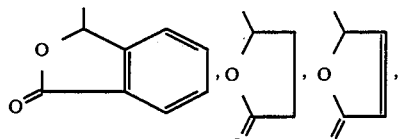

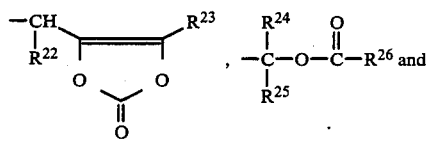

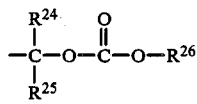

where
$R^{22}$ and $R^{23}$ are identical or different and
stand for hydrogen, phenyl or
for $C_1$–$C_4$-alkyl, preferably for methyl,
$R^{24}$ and $R^{25}$ are identical or different and
stand for hydrogen or
for $C_1$–$C_4$-alkyl, preferably methyl, and
$R^{26}$ - stands for $C_1$–$C_6$-alkyl, preferably for $C_1$–$C_4$-alkyl.

The compounds of the formula I can be present as free acids, esters, as internal salts or as non-toxic pharmaceutically tolerable salts of the acidic carboxyl groups, such as sodium salts, potassium salts, magnesium salts, calcium salts, aluminum salts or ammonium salts, with amines such a di- or tri-lower alkylamines, procaine, dibenzylamine, N,N'-dibenzylethylenediamine, N-benzyl-β-phenyl-ethylamine, N-methyl and N-ethylmorpholine, 1-ephenamine, dihydroabietylamine, N,N'-bis-dehydroabietylethylenediamine, N-lower alkylpiperidine and other amines which can be used for formation of salts of penicillins and cephalosporins.

On account of the presence of the asymmetric carbon atom denoted by *, the new β-lactam antibiotics of the formula (I) include the D-, L- and D,L-form. The D-forms of the compounds of the general formula (I) according to the invention are preferred.

Both the mixture of diastereomers and the D-form and L-form of the compounds according to the invention can be employed for the treatment of bacterial infectious diseases.

Compounds of the general formula (I) may be mentioned as preferred, in which
$R^1$ - stands for a group of the formula

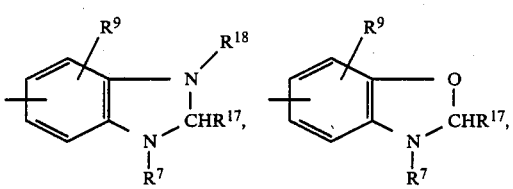

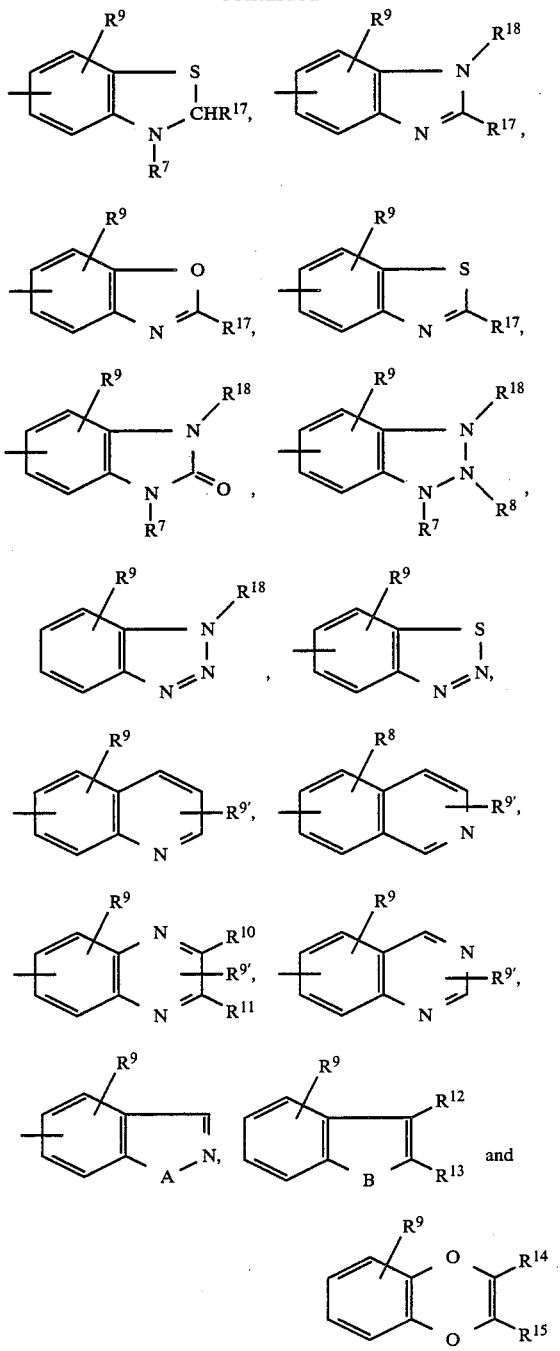

wherein

R[7] - stands for hydrogen, or stands for hydroxyl or amino, or stands for straight-chain, branched or cyclic alkyl or alkenyl each having up to 8 carbon atoms, each of which is optionally substituted by one or more fluorine, chlorine, bromine, optionally substituted amino, hydroxyl or phenyl, or stands for optionally substituted phenyl R[8] stands hydrogen, or stands fox optionally substituted phenyl or stands for straight-chain, branched or cyclic alkyl or alkenyl each having up to 8 carbon atoms, each of which is optionally substituted by one or more fluorine, chlorine, bromine alkoxy having up to 4 carbon atoms, hydroxyl, carboxyl, phenyl, sulpho or an optionally substituted amino group, R[9] and R[9'] are dentical or different and stand for hydrogen, or stand for straight-chain or branched alkyl, alkoxy or alkylthio each having up to 6 carbon atoms, or stand for trifluoromethyl or trifluoromethoxy, or stand for hydroxyl, mercapto, nitro, cyano, fluorine, chlorine or bromine, or stand for an optionally substituted amino group, R[10] and R[11] are identical or different and stand for hydrogen, or stand for phenyl which is optionally monosubstituted or disubstituted by identical or different fluorine, chlorine, bromine, alkyl, alkoxy or alkylthio each having up to 4 carbon atoms, halogenoalkyl, halogenoalkoxy or halogenoalkylthio each having up to 3 carbon atoms and having one to three fluorine, by nitro, cyano, amino or dimethylamino, or stand for an optionally substituted amino group having the abovementioned meaning, or stand for hydroxyl or alkoxy having up to 6 carbon atoms, or stand for benzyloxy or alkanoyloxy having up to 4 carbon atoms, or stand for straight-chain, branched or cyclic alkyl having up to 8 carbon atoms, which is optionally substituted by one or more fluorine, chlorine, bromine, alkoxy or alkylthio each having up to 4 carbon atoms, halogenoalkoxy or halogenoalkylthio each having up to 4 carbon atoms and one to three fluorine, nitro, cyano, an optionally substituted amino group having the abovementioned meaning, phenyl, sulpho, sulphamoyl, alkylsulphonyl having up to 2 carbon atoms, hydroxyl, mercapto, benzoyloxy, alkanoyloxy having up to 4 carbon atoms, carbamoyloxy or alkoxycarbonyl having up to 4 carbon atoms, R[12] and R[13] are identical or different and stand for hydrogen, or stand for phenyl which is optionally monosubstituted or disubstituted by identical or different fluorine, chlorine, bromine, alkyl, alkoxy or alkylthio each having up to 4 carbon atoms, halogenoalkyl, halogenoalkoxy, halogenoalkylthio each having up to 3 carbon atoms and having one to three fluorine, by nitro, cyano, dimethylamino or amino, or stand for hydroxyl, or stand for pyridyl, thienyl, furyl or pyrimidyl, or stand for an optionally substituted amino group having the abovementioned meaning, or stand for straight-chain, branched or cyclic alkoxy having up to 6 carbon atoms, or stand for benzoyloxy or alkanoyloxy having up to 4 carbon atoms, or stand for benzoyl or acetyl, or stand for alkoxycarbonyl having up to 6 carbon atoms, or stand for straight-chain, branched or cyclic alkyl having up to 8 carbon atoms, which is optionally substituted by one to three fluorine, chlorine, bromine, alkoxy or alkylthio each having up to 4 carbon atoms, halogenoalkoxy or halogenoalkylthio each having up to 4 carbon atoms and having one to three fluorine, nitro, cyano, an optionally substituted amino group having the abovementioned meaning, phenyl, sulpho, sulphamoyl, alkylsulphonyl having up to 2 carbon atoms, hydroxyl, mercapto, benzyloxy, alkanoyloxy having up to 4 carbon atoms, carbamoyloxy, alkoxycarbonyl having up to 4 carbon atoms, phenyloxy, phenylthio, benzyloxy or benzylthio, or $R^{12}$ and $R^{13}$ together stand for a grouping of the formula

$R^{14}$ and $R^{15}$ are identical or different and
stand for hydrogen, or
stand for straight-chain, branched or cyclic alkyl having up to 8 carbon atoms, which is optionally substituted by one or more fluorine, chlorine, bromine, alkoxy or alkylthio each having up to 4 carbon atoms, halogenoalkoxy or halogenoalkylthio each having up to 4 carbon atoms and having one to three fluorine, nitro, cyano, an optionally substituted amino group having the abovementioned meaning, phenyl, sulpho, sulphamoyl, alkylsulphonyl having up to 2 carbon atoms, hydroxyl, mercapto, benzoyloxy, alkanoyloxy having up to 4 carbon atoms, carbamoyloxy or alkoxycarbonyl having up to 4 carbon atoms, or
stand for phenyl which is optionally monosubstituted or disubstituted by identical or different fluorine, chlorine, bromine, alkyl, alkoxy or alkylthio each having up to 4 carbon atoms, halogenoalkyl, halogenoalkoxy or halogenoalkylthio each having up to 3 carbon atoms and one to three fluorine, nitro, cyano, amino or dimethylamino, or
stand for alkoxycarbonyl having up to 6 carbon atoms, A - stands for O, S or $-NR^{19}$,
B - stands for O or $-NR^{16}$,
$R^{16}$ stands for hydrogen, or
for phenyl, or
for straight-chain, branched or cyclic alkyl having up to 6 carbon atoms,
$R^{17}$ has the same meaning as $R^8$ and in addition
stands for fluorine, chlorine or bromine, or
stands for alkoxy, alkylthio or alkylsulphonyl each having up to 6 carbon atoms, or
stands for an optionally substituted amino group, or
stands for phosphono, sulpho, sulphamoyl, hydroxyl, mercapto, phenylthio or phenyloxy, or
stands for guanidino, hydrazino or hydroxylamino, or
stands for optionally substituted heterocyclyl, heterocyclyloxy or heterocyclylthio,
$R^{18}$ has the same meaning as $R^{17}$, but does not complete a double bond with $R^8$, or
$R^{17}$ and $R^{18}$ together stand for a $C_2$-$C_4$-methylene chain which is optionally interrupted by sulphur, and
$R^{19}$ has the same meaning as $R^{16}$ and can be identical or different to this,
$R^2$ - stands for hydrogen, or
for methoxy, or
stands for formamido or hydroxylamino,
$R^3$ - stands for hydrogen, hydroxyl, alkyl or alkoxy having up to 4 carbon atoms, $R^4$ - stands for hydrogen, chlorine, fluorine, methyl, methoxy, methylthio, trifluoromethyl, methoxymethyl, vinyl, carbamoyloxymethyl or acetyoxymethyl, or
denotes a group of the formula $-CH=CH-CH_3$, $-CH=CH-C_2H_5$, $-CH=CH-CH_2Cl$, $-CH=CH-CF_3$, $-CH=CH-CH_2OCH_3$,

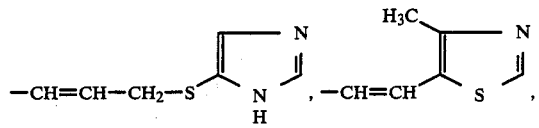

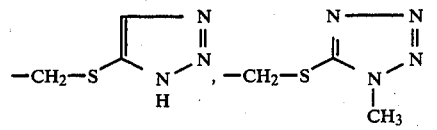

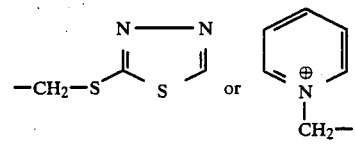

and $R^5$ - stands for hydrogen, or
stands for methyl, ethyl, tert.-butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl 1-phenoxyethyl, 2-methyl-2-propenyl, 4-benzyl, 2-nitrobenzyl, trimethylsilylethyl or tert.-butyldimethylsilylethyl, or
stands for a radical of the formula

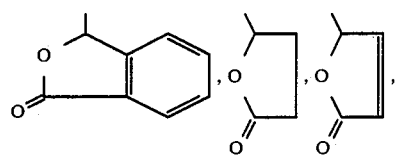

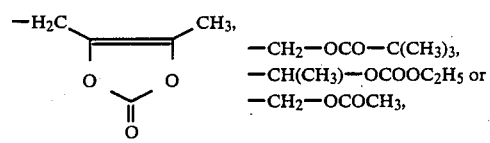

and
$R^6$ - stands for hydrogen, and their pharmaceutically tolerable salts.

Compounds of the general formula (I) may be mentioned as particularly preferred, in which
$R^1$ - stands for a group of the formula

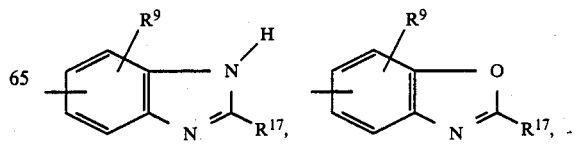

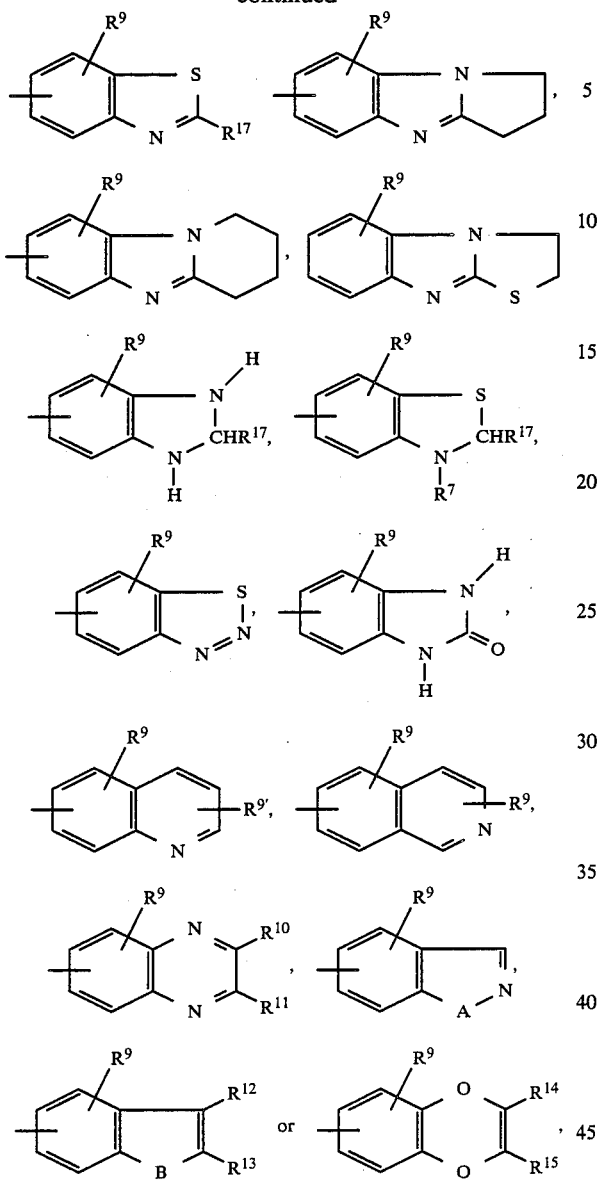

wherein

R[7] - stands for hydrogen, or
stands for straight-chain, branched or cyclic alkyl or alkenyl having up to 6 carbon atoms, each of which is optionally substituted by fluorine amino, hydroxyl or phenyl, or
stands for optionally substituted phenyl, R[9] and R[9'] are identical or different and
stand for hydrogen, or
stand for straight-chain or branched alkyl, alkoxy or alkylthio each having up to 4 carbon atoms, or
stand for trifluoromethyl or trifluoromethoxy, or
stand for hydroxyl, nitro, cyano, fluorine or chlorine, or
stand for amino, methylamino, dimethylamino, phenylamino or acetylamino, R[10] and R[11] are identical or different and stand for hydrogen, or
stand for phenyl which is optionally substituted by chlorine, fluorine, alkyl having up to 4 carbon atoms, methoxy, methylthio, trifluoromethyl, trifluoromethoxy, trifluoromethylthio, nitro, cyano, amino or dimethylamino, or
stand for amino, methylamino, dimethylamino, phenylamino or acetylamino, or
stand for hydroxyl, or
stand for alkoxy having up to 4 carbon atoms, or
stand for benzoyloxy or acetyloxy, or
stand for straight-chain, branched or cyclic alkyl or alkenyl each having up to 6 carbon atoms, each of which can be substituted by fluorine, chlorine, methoxy, methylthio, trifluoromethoxy or cyano, R[12] and R[13] are identical or different and
stand for hydrogen, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for pyridyl, thienyl, furyl pyrimidyl or hydroxyl, or
stand for amino, methylamino, dimethylamino, phenylamino or acetylamino, or
stand for alkoxy having up to 4 carbon atoms, or
stand for benzoyloxy or acetyloxy or
stand for benzoyl or acetyl, or
stand for alkoxycarbonyl having up to 4 carbon atoms, or
stand for straight-chain, branched or cyclic alkyl or alkenyl having up to 6 carbon atoms, each of which is optionally substituted by fluorine, chlorine, methoxy, methylthio, trifluoromethoxy, cyano, phenyloxy or benzyloxy, R[14] and R[15] are identical or different and
stand for hydrogen, or
stand for straight-chain, branched or cyclic alkyl or alkenyl having up to 6 carbon atoms, each of which is optionally substituted by fluorine, chlorine, methoxy, methylthio, trifluoromethoxy or cyano, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for alkoxycarbonyl having up to 4 carbon atoms, A - stands for O, S or —NR[19],
B - stands for O or —NR[16],
R[16] stands for hydrogen, or
stands for phenyl, or
stands for straight-chain or branched alkyl having up to 4 carbon atoms,
R[17] stands for hydrogen, or
stands for straight-chain or branched alkyl or alkenyl each having up to 4 carbon atoms, each of which is optionally substituted by fluorine, chlorine, alkoxy having up to 4 carbon atoms, hydroxyl, carboxyl, phenyl, sulpho, amino, alkylamino or dialkylamino each having up to 3 carbon atoms per alkyl group, phenylamino,
stands for fluorine, chlorine or bromine, or
stands for alkoxy or alkylthio each having up to 4 carbon atoms, or
stands for phenyl, or
stands for amino, alkylamino or dialkylamino each having up to 3 carbon atoms per alkyl group, phenylamino, benzylamino or acetylamino, or stands for alkylsulphonyl having up to 4 carbon atoms, or stands for sulpho or sulphamoyl, or stands for hydroxyl, mercapto, phenyloxy or phenylthio, or stands for guanidino, hydrazino or hydroxylamino, or stands for pyrrolyl, pyrrolidinyl, pyrazolyl, imidazolyl, pyridyl, quinolyl, isoquinolyl, furyl, thienyl, morpholinyl, piperidinyl, piperazinyl or pyrimidyl, each of which can be substituted by fluorine, chlorine, methyl, nitro, cyano, hydroxyl, trifluoromethyl, methoxy or amino, or stands for pyridylthio or pyridyloxy, $R^{18}$ - has the same meaning as $R^{17}$ and can be identical or different to this and $R^{19}$ - has the same meaning as $R^{16}$ and is identical or different to this, $R^2$ - stands for hydrogen, or stands for methoxy, or stands for formamido or hydroxylamino, $R^3$ - stands for hydrogen, hydroxyl, methyl or methoxy, $R^4$ - stands for hydrogen, chlorine, methyl, methoxy, methoxymethyl, vinyl, cis-propenyl or acetyloxymethyl, or $R^5$ - stands for hydrogen, or stands for a radical of the formula —CH$_2$—OCOCH$_3$,

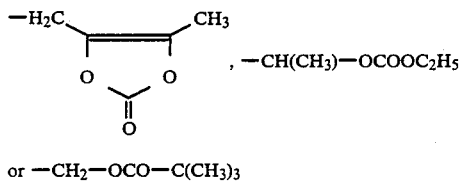

or —CH$_2$—OCO—C(CH$_3$)$_3$ and $R^6$ - stands for hydrogen, and their pharmaceutically tolerable sodium salts.

Moreover, a process for the preparation of the heteroanellated phenylglycine-β-lactam antibiotics of the general formula (I) according to the invention has been found, which is characterized in that carboxylic acids of the general formula (II)

in which $R^1$ and $R^6$ have the abovementioned meaning, are reacted, after activation of the carboxyl group by conversion into a mixed anhydride, for example using ethyl chloroformate or isobutyl chloroformate or methanesulphonyl chloride, or by converting into the acid halide, or by converting into an activated ester, for example using dicyclohexylcarbodiimide (DCC), if appropriate in the presence of N-hydroxybenzotriazole, with the β-lactam amines of the general formula (III)

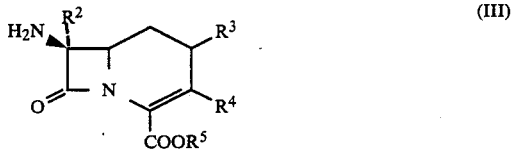

in which $R^2$, $R^3$, $R^4$ and $R^5$ have the abovementioned meaning, and then, if desired, eliminating protecting groups and preparing the desired salts or the free acids from the salts.

The process according to the invention can be illustrated by the following equation:

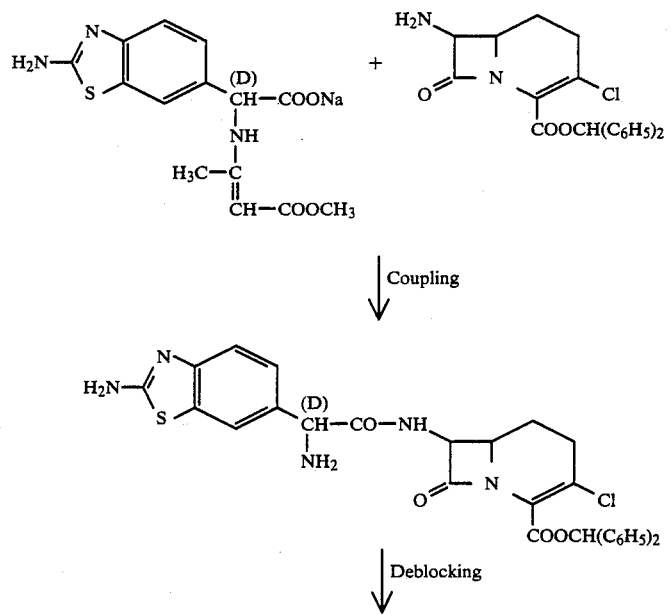

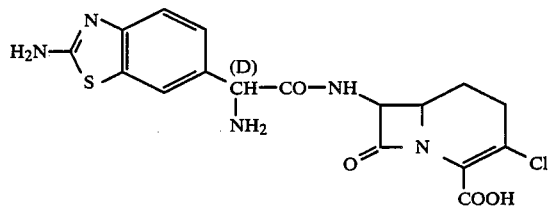

When carrying out the process, it has proved advantageous to activate the carboxylic acid and then to couple it with the β-lactam amines which are brought into solution as salts with amine. Activation using sulphonic acid derivatives of the general formula (IV) or using chloroformates, preferably ethyl chloroformate, to give anhydrides of the general formula (Va, b), as is illustrated in the following equation, is particularly advantageous.

is likewise possible to employ mixtures of the solvents mentioned, if appropriate mixed with water.

Suitable amines are tertiary amines such as, for example, triethylamine, ethyldiisopropylamine or tributylamine, but also sterically hindered secondary amines such as, for example, diisopropylamine. Mixtures of the solvents mentioned can likewise be employed.

The reaction can be carried out at temperatures between −80° C. and room temperature. The activation is

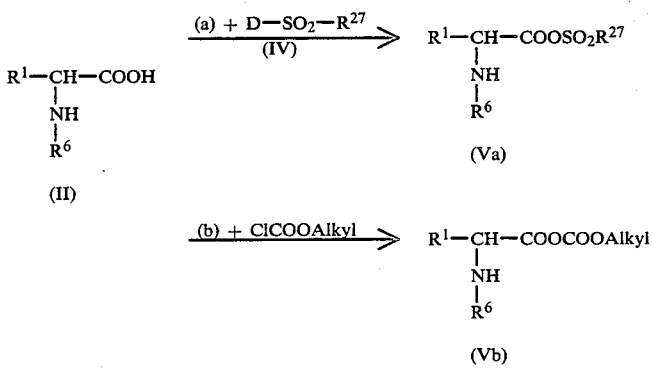

In this connection, in the formula (IV) or (Va) D - stands for the radical $$R^{27}-SO_2-O- \text{ or halogen}$$

and $R^{27}$ - stands for alkyl having up to 10 carbon atoms, which is optionally substituted by fluorine, chlorine, cyano, phenyl, alkoxycarbonyl or alkoxy each having up to 4 carbon atoms, or stands for phenyl which is optionally substituted by fluorine, chlorine, bromine, cyano, alkyl, alkoxy, alkylthio, alkoxycarbonyl or alkylcarbonyl each having up to 4 carbon atoms, nitro, trifluoromethyl or phenyl, If $R^{27}$ is substituted, one to three substituents, particularly preferably those mentioned above, are present.

Very particularly preferably, $R^{27}$ represents a methyl or p-tolyl radical.

The mixed anhydrides of the general formula (Va, b) are prepared by dissolving the carboxylic acids of the general formula (II) and 1 to 1.4 equivalents of an amine in a solvent and allowing the solution to react with 1 to 1.2 equivalents of a sulphonic acid derivative of the formula (IV) or a chloroformate.

Suitable solvents are all solvents which do not change under the reaction conditions. These preferably include ethers such as, for example, diethyl ether, dioxane or tetrahydrofuran, or chlorinated hydrocarbons such as methylene chloride, chloroform or carbon tetrachloride, or amides such as dimethylformamide or hexamethylphosphoric triamide, or acetonitrile, or acetone. It advantageously carried out with methanesulphonyl chloride in dimethylformamide at −40° C. to −60° C.

The solvents mentioned in the preparation of the compound of the formula (V) or water can be used to dissolve the β-lactam amines of the general formula (III), and the amines mentioned there can be used as bases.

Activation of the carboxylic acid of the general formula (II) by converting into an activated ester using, for example, dicyclohexylcarbodiimide, if appropriate in the presence of N-hydroxysuccinimide or 1-hydroxybenzotriazole, is also particularly advantageous.

Suitable solvents in this connection are all solvents which are also suitable for the preparation of anhydrides of the general formula (V) and have already been listed there. The reactions can be carried out at temperatures between −30° C. and +100° C. Activation is advantageously carried out for 2 to 6 hours using 1-hydroxybenzotriazole and dicyclohexylcarbodiimide in dimethylformamide at room temperature. The product is then filtered off with suction from the deposited dicyclohexylurea and reacted in the course of 2 to 24 hours with the β-lactam amine of the general formula (III) in the form of a solution of its amine salt. The solvents mentioned in the preparation of the compound of the formula (V) can be used to dissolve the β-lactam amines of the general formula (III) and the amines mentioned there can be used as bases.

The carboxylic acids of the general formula (II) employed as starting compounds are known or can be prepared by known methods [DE-OS (German Published Specification) No. 3,509,618; DE-OS (German Published Specification) No. 3,508,258].

The β-lactam amines of the general formula (III) employed as starting substances are known or can be prepared by known methods [EP-PS Nos. 0,154,253; 0,025,602; 0,027,882; 0,075,805; 0,014,475; 0,014,476; Chem. Pharma. Bull. 28, (5), 1563 (1980)].

The stereochemically homogeneous D- or L-forms of the compounds of the formula (I) according to the invention are obtained when the mixtures of diastereomers are separated by HPLC chromatography.

On the other hand, the pure D- or L-form (preferably the D-form) is obtained when a chemical racemate separation, for example using dihydroabietylamine, phenylethylamine or camphorsulphonic acid, or a racemate separation, for example via N-acetyl-amino acid derivatives, for example using subtilisin, penicillin acylase or porcine renal acylase has already been carried out at the stage of the racemic amino acid of the formula (II) and the stereochemically homogeneous D- or L-forms of the compounds of the formula (II) are subsequently reacted in the manner indicated.

In addition to the experimental examples, the following compounds may be mentioned in detail as new active compounds according to the invention from the cephalosporin series:

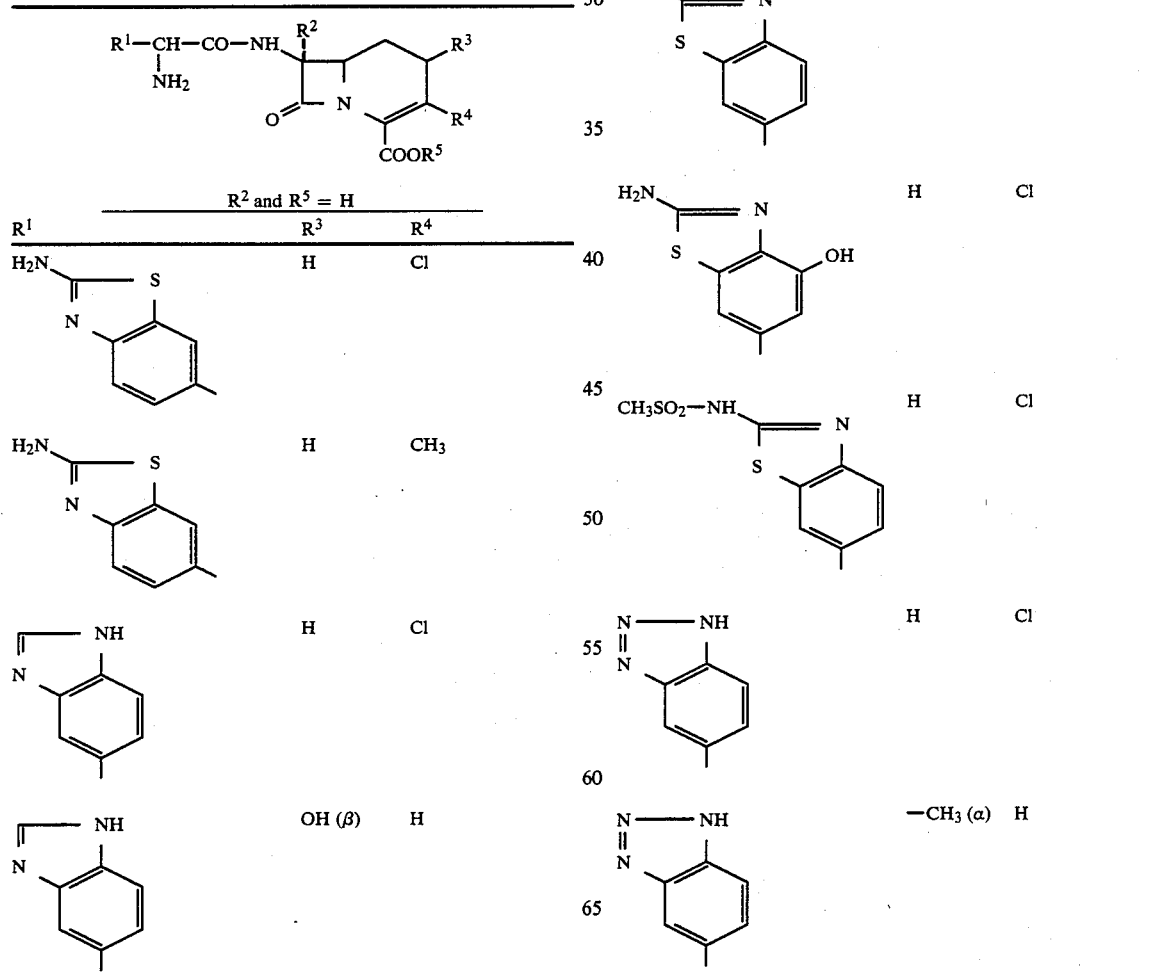

TABLE 1-continued

R¹—CH(NH₂)—CO—NH— [β-lactam fused ring with R², R³, R⁴, COOR⁵]

R² and R⁵ = H

| R¹ | R³ | R⁴ |
|---|---|---|
| H₂N-C(=N-)-S- (2-amino-thiazolyl connected to phenyl, 4-methyl) | OH (β) | H |
| H₂N-C(=N-)-S- (2-amino-thiazolyl connected to phenyl, 4-methyl) | H | —CH=CH—CH₃ (cis) |
| (CH₃)(H₃C)C=N—/N= (diazabutadiene on phenyl, 4-methyl) | H | Cl |
| quinolinyl (6-methyl) | H | Cl |
| indolyl-NH (methylphenyl) | H | Cl |
| pyrrolyl (NH, methylphenyl) | H | Cl |
| S=CH—N= (methylphenyl) | H | Cl |
| N=N-S- (thiadiazolyl-phenyl, 4-methyl) | OH (β) | H |
| indoline-N-H (methylphenyl) | H | —CH=CH—CH₃ (cis) |
| indoline-N-H (methylphenyl) | H | —CH=CH—CH₃ (cis) |
| H₂N-C(=N-)-O- (2-amino-oxazolyl-phenyl, 4-methyl) | H | Cl |
| H₂N-C(=N-)-O- (2-amino-oxazolyl-phenyl, 4-methyl) | —CH₃ (β) | H |
| H-C(=N-)-S- (thiazolyl-phenyl, 4-methyl) | H | Cl |
| H₂N-C(=N-)-S- (2-amino-thiazolyl-phenyl, 4-methyl) | —CH₃ (α) | H |

The following carbacephem derivatives may be mentioned in detail as active compounds:

(6R, 7S)-(D)-7-[(2-aminobenzothiazol-5-yl)glycylamido]-3-chloro-1-azabicyclo[4,2,0]oct-2-en-8-one-2-carboxylic acid (6R, 7S)-(D)-7-[(benzimidazol-5(6)-yl)glycylamido]-3-chloro-1-azabicyclo[4,2,0]oct-2-en-8-one-2-carboxylic acid (6R, 7S)-(D)-7-[(benzimidazol-5(6)-yl)glycylamido]-4B-hydroxy-1-azabicyclo[4,2,0]oct-2-en-8-one-2-carboxylic acid (6R, 7S)-(D)-7-[(2-amino-1H-benzimidazol-5(6)-yl)glycylamido]-4β-hydroxy-1-azabicyclo[4,2,0]oct-2-en-8-one-2-carboxylic acid (6R, 7S)-(D)-7-[(2-methyl-1H-benzimidazol-5-yl)glycylamido]-3-chloro-1-azabicyclo[4,2,0]oct-2-en-8-one-2-carboxylic acid (6R, 7S)-(D)-7-[(2-cyclopropyl-benzothiazol-6-yl)glycylamino]-3-chloro-1-azabicyclo[4,2,0]oct-2-en-8-one-2-carboxylic acid (6R, 7S)-(D)-7-[(2-amino-4-hydroxy-benzothiazol-6-yl)glycylamido]-3-chloro-1-azabicyclo[4,2,0]oct-2-en-8-one-2-carboxylic acid (6R, 7S)-(D)-7-[(benzotriazol-5(6)-yl)glycylamido]-3-chloro-1-azabicyclo[4,2,0]oct-2-en-8-one-2-carboxylic acid (6R, 7S)-(D)-7-[(benzotriazol-7(6)-yl)glycylamido]-4α-methyl-1-azabicyclo[4,2,0]oct-2-en-8-one-2-carboxylic acid (6R, 7S)-(D)-7-[(2-aminobenzothiazol-6-yl)glycylamido]-4β-hydroxy-1-azabicyclo[4,2,0]oct-2-en-8-one-2-carboxylic acid (6R, 7S)-(D)-7-[(2-aminobenzothiazol-6-yl)glycylamido]-3-[(Z)-1-propen-1-yl]-1-azabicyclo[4,2,0]oct-2-en-8-one-2-carboxylic acid (6R, 7S)-(D)-7-[(2,3-dimethylquinoxalin-6-yl)-glycylamido]-3-chloro-1-azabicyclo[4,2,0]oct-2-en-8-one-2-2-carboxylic acid (6R, 7S)-(D)-7-[(2,3-dimethylquinoxalin-6-yl)-glycylamido]-3-chloro-1-azabicyclo[4,2,0]oct-2-en-8-one-2-carboxylic acid (6R, 7S)-(D)-7-[(quinol-6-yl)glycylamido]-3-chloro-1-azabicyclo[4,2,0]oct-2-en-8-one-2-carboxylic acid (6R, 7S)-(D)-7-[(indol-5-yl)glycylamido]-3-chloro-1-azabicyclo[4,2,0]oct-2-on-8-one-2-carboxylic acid (6R, 7S)-(D)-7-[(indol-6-yl)glycylamido]-3-chloro-1-azabicyclo[4,2,0]oct-2-en-8-one-2-carboxylic acid (6R, 7S)-(D)-7-[(2,1-benzisothiazol-6-yl)glycylamido]-3-chloro-1-azabicyclo[4,2,0]oct-2-en-8-one-2-carboxylic acid (6R, 7S)-(D)-7-[1,2,3-benzothiadiazol-6-yl)glycylamido]-4-8-hydroxy-1-azabicyclo[4,2,0]oct-2-en-8-one-2-carboxylic acid (6R, 7S)-(D)-7-[(indolin-5-yl)-glycylamido]-3-[(Z)-1-propen-1-yl]-1-azabicyclo[4,2,0]oct-2-en-8-one-2-carboxylic acid (6R, 7S)-(D)-7-[(indol-5-yl)glycylamido]-3-[(Z)-1-propen-1-yl]-1-azabicyclo[4,2,0]oct-2-en-8-one-2-carboxylic acid (6R, 7S)-(D)-7-[(2-aminobenzoxazol-6-yl)glycylamido]-3-chloro-1-azabicyclo[4,2,0]oct-2-en-8-one-2-carboxylic acid (6R, 7S)-(D)-7-[(2-aminobenzoxazol-6-yl)glycylamido]-4β-methyl-1-azabicyclo[4,2,0]oct-2-en-8-one-2-carboxylic acid (6R, 7S)-(D)-7-[(benzothiazol-6-yl)glycylamido]-3-chloro-1-azabicyclo[4,2,0]oct-2-en-8-one-2-carboxylic acid (6R, 7S)-(D)-7-[(2-aminobenzothiazol-6-yl)glycylamido]-4α-methyl-1-azabicyclo[4,2,0]oct-2-en-8-one-2-carboxylic acid The compounds of the general formula I according to the invention exhibit a wide antibacterial spectrum against gram-positive and gram-negative bacteria, combined with low toxicity. These properties make possible their use as chemotherapeutic active compounds in human and veterinary medicine.

The compounds according to the invention are active against a very wide spectrum of microorganisms. Gram-negative and gram-positive bacteria and bacteria-like microorganisms can be controlled with their aid, and the diseases produced by these pathogens can also be prevented, improved and/or cured.

The compounds according to the invention are particularly active against bacteria and bacteria-like microorganisms. They are therefore particularly well suited in human and veterinary medicine for the prophylaxis and chemotherapy of local and systemic infections which are produced by these pathogens.

For example, local and/or systemic diseases which are caused by the following pathogens or by mixtures of the following pathogens can be treated and/or prevented: gram-positive cocci, for example staphylococci (*Staph. aureus, Staph. epidermis*) and streptococci (*Strept. agalactiae, Strept. faecalis, Strept. pneumoniae, Strept. pyogenes*); gram-negative cocci (*Neisseria gonorrhoeae*) and also gram-negative rods such as Enterobacteriaceae, for example *Escherichia coli, Haemophilus influenzae,* Citrobacter (*Citrob. freundii, Citrob. divernis*), Salmonella and Shigella; furthermore Klebsiella (*Klebs. pneumoniae, Klebs. oxytoca*), Enterobacter (*Ent. aerogenes, Ent. agglomerans*), Hafnia, Serratia (*Serr. marcescens*), Proteus (*Pr. mirabilis, Pr. rettgeri, Pr. vulgaris*), Providencia, Yersinia, and also the order Acinetobacter. Moreover, the antibacterial spectrum comprises the order Pseudomonas (*Pr. aeruginosa, Ps. maltophilia*) and also strictly anaerobic bacteria such as, for example, *Bacteroides fragilis,* representatives of the order Peptococcus, Peptostreptococcus and also the order Clostridium; furthermore mycoplasma (*M. pneumoniae, M. hominis, M. urealyticum*) and also mycobacteria, for example *Mycobacterium tuberculosis. The substances according to the invention act in particular against staphylococci, streptococci, enterococci and Haemophilus influenzae.* On parenteral or, in particular, oral administration, the new compounds are highly active against microorganisms such as staphylococci, streptococci, Enterobacteriaceae, *Escherichia coli,* Klebsiella, Salmonella, Shigella and Proteus.

The above enumeration of pathogens is merely for example and in no way to be conceived as limiting. Examples of diseases which may be caused by the said pathogens or mixed infections and which may be prevented, improved or cured by the compounds according to the invention are, for example:

Infectious diseases in humans, such as, for example, otitis, pharyngitis, pneumonia, peritonitis, pyelonephritis, cystitis, endocarditis, systemic infections, bronchitis (acute, chronic), septic infections, diseases of the upper airways, diffuse panbronchiolitis, pulmonary emphysema, dysentery, enteritis, hepatic abscesses, urethritis, prostatitis, epididymitis, gastrointestinal infections, bone and joint infections, cystic fibrosis, skin infections, post-operative wound infections, abscesses, phlegmon, wound infections, infected burns, scalds, infections in the oral region, infections after dental operations, osteomyelitis, septic arthritis, cholecystitis, peritonitis with appendicitis, cholangitis, intra-abdominal abscesses, pancreatitis, sinusitis, mastoiditis, mastitis, tonsillitis, typhus, meningitis and infections of the nervous systems, salpingitis, endometritis, genital infections, pelviperitonitis and eye infections.

In addition to humans, bacterial infections can also be treated in other species. Examples which may be mentioned are:

pig: coli-diarrhoea, enterotoxaemia, sepsis, dysentery, salmonellosis, metritis-mastitis-agalactia syndrome, mastitis; ruminants (cow, sheep, goat): diarrhoea, sepsis, bronchopneumonia, salmonellosis, pasteurellosis, mycoplasmosis, genital infections;

horse: bronchopneumonia, joint-ill, puerperal and postpuerperal infections, salmonellosis;

dog and cat; bronchopneumonia, diarrhoea, dermatitis, otitis, urinary tract infections, prostatitis;

poultry (hen, turkey, quail, pigeon, ornamental birds, others): mycoplasmosis, E. coli infections, chronic airway diseases, salmonellosis, pasteurellosis, psittacosis.

Bacterial diseases in the rearing and keeping of productive and ornamental fish can likewise be treated, where the antibacterial spectrum is widened beyond the previously mentioned pathogens to further pathogens such as, for example, Pasteurella, Brucella, Campylobacter, Listeria, Erysipelothrix, Corynebacteria, Borellia, Treponema, Nocardia, Rikettsia and Yersinia.

The present invention includes pharmaceutical preparations which contain one or more active compounds according to the invention or which consist of one or more active compounds according to the invention in addition to non-toxic, inert pharmaceutically suitable excipients and processes for the production of these preparations.

The present invention also includes pharmaceutical preparations in dosage units. This means that the preparations are in the form of individual portions, for example tablets, dragees, capsules, pills, suppositories and ampules whose active compound content corresponds to a fraction or a multiple of an individual dose. The dosage units may contain, for example, 1, 2, 3 or 4 individual doses or $\frac{1}{2}$, $\frac{1}{3}$ or $\frac{1}{4}$ of an individual dose. An individual dose preferably contains the amount of active compound which is administered in one application and which usually corresponds to a whole, a half, a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders or sprays.

Tablets, dragees, capsules, pills and granules may contain the active compound(s) in addition to the customary excipients, such as (a) fillers and extenders, for example starches, lactose, sucrose, glucose, mannitol and silica, (b) binders, for e ample carboxymethylcellulose, alginates, gelatin, polyvinylpyrrolidone, (c) humectants, for example glycerol, (d) disintegrants, for example agar-agar, calcium carbonate and sodium carbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be provided with the customary coatings and shells containing, if appropriate, opacifying agents and can be so composed that they release the active compound(s), if appropriate with a delay, only or preferably in a certain part of the intestinal tract, in which case, for example, oolymeric substances and waxes can be used as embedding materials.

If appropriate, the active compound(s) may also be present in micro-encapsulated form with one or more of the abovementioned excipients.

In addition to the active compound(s), suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances.

Ointments, pastes, creams and gels may contain the customary excipients in addition to the active compound(s), for example animal and vegetable fats, waxes, paraffins, starch, tragacanth, cellulose derivatives, polyethylene glycols, silicones, bentonites, silica, talc and zinc oxide or mixtures of these substances.

Powders and sprays may contain the customary excipients in addition to the active compound(s), for example lactose, talc, silica, aluminum hydroxide, calcium silicate and polyamide powder or mixtures of these substances. Sprays may additionally contain the customary propellants, for example chlorofluorohydrocarbons.

Solutions and emulsions may contain the customary excipients, such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound(s).

The formulation forms mentioned may also contain colorants, preservatives and also odor-improving and flavour-improving additives, for example peppermint oil and eucalyptus oil and sweeteners, for example saccharine.

The therapeutically active compounds should preferably be present in the abovementioned pharmaceutical preparations in a concentration of about 0.1 to 99.5, preferably 0.5 to 95% by weight, of the total mixture.

The abovementioned pharmaceutical preparations may also contain further pharmaceutical active compounds in addition to the active compounds according to the invention.

The preparation of the abovementioned pharmaceutical preparations takes place in a customary manner by known methods, for example by mixing the active compound(s) with the excipient(s).

The preparations mentioned may be used in humans and animals either orally, rectally, parenterally (intravenously, intramuscularly, subcutaneously), intracisternally, intravaginally, interperitoneally, locally (powders, ointments, drops) and for the therapy of infections in hollow spaces and body cavities. Suitable preparations are injection solutions, solutions and suspensions for oral therapy, gels, pour on formulations, emulsions, ointments or drops. For local therapy, ophthalmological and dermatological formulations, silver salts and other salts, ear drops, eye ointments, powders or solutions may be used. In animals, the administration may also take place in suitable formulations via the feed or drinking water.

Furthermore, gels, powders, tablets, delayedrelease tablets, premixes, concentrates, granules, pellets, tablets, boli, capsules, aerosols, sprays and inhalants may be used in humans and animals. Furthermore, the compounds according to the invention may be incorporated into other excipients such as, for example, plastics (plastic chains for local therapy), collagen or bone cement In general, it has proved advantageous both in human and veterinary medicine to administer the active compound(s) in total amounts of about 0.5 to about 500, preferably 5 to 100 mg/kg of body weight every 24 hours, if appropriate in the form of several individual doses, to attain the desired results. An individual dose preferably contains the active compound(s) in amounts of about 1 to about 80, in particular 3 to 30 mg/kg of body weight. However, it may be necessary to depart from the dosages mentioned, depending on the type and the body weight of the subject to be treated, the nature and severity of the disease, the type of composition and the administration of the medicament and also the time period or interval within which the administration takes place.

Thus in some cases it may be sufficient to manage with less than the abovementioned amount of active compound, whereas in other cases the abovementioned amount of active compound must be exceeded. The optimum dosage required in each case and the type of administration of the active compound can easily be established by one skilled in the art on the basis of his expert knowledge.

The new compounds may be combined, in the customary concentrations and preparations, together with the feed or lactamase inhibitors, for example with penicillins which are particularly resistant to penicillinase and with clavulanic acid. Such a combination could be, for example, that with oxacillin or dicloxacillin.

The compounds according to the invention can also be combined with aminoglycoside antibiotics, such as, for example, gentamicin, sisomicin, kanamicin, amikacin or tobramicin, for the purpose of widening the spectrum of action and in order to achieve an increase in action.

Preparation Examples

EXAMPLE 1

(6S, 7S)-(D)-[(2-aminobenzothiazol-6-yl)glycylamido]-3-chloro-1-azabicyclo[4,2,0]oct-2-en-8-one-2-carboxylic acid

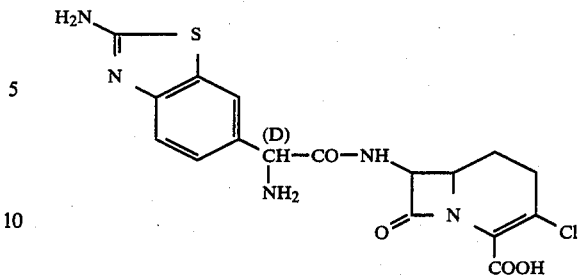

(a) Activation of the precursor acid:

547 mg [corresponds to 520 mg (1.44 mmol) of pure material; 1.3 equivalents] of sodium D-α-[(1-methyl-2-methoxycarbonylvinyl)-amino]-(2-aminobenzothiazol-6-yl)acetate are dissolved in 4 ml of dimethylformamide and 1.5 ml of acetonitrile to give a clear solution. The solution is then cooled to −60° C. and 1 drop of 3-dimethylamino-1-propanol and 0.138 ml of ethyl chloroformate are added successively and the mixture is stirred for 30 minutes at −60° C.

(b) Preparation of the carbacephem component:

0.300 mg (1.10 mmol) of t-butyl (±)-cis-7-amino-3-chloro-1-azabicyclo-[4,2,0]oct-2-en-8-one-2-carboxylate [see EP Pat. No. 0,014,476, Kyowa Hakko Kogyo Co. Ltd.] are dissolved in 4 ml of dimethylformamide and 0.8 ml of acetonitrile and 0.3 ml of water is added at 0° C.

(c) Coupling:

The carbacephem solution (b) cooled to 0° C. is added slowly to the solution of the mixed anhydride (a) at −60°C., during which the temperature rises from −60° C. to −30° C. The mixture is stirred for a total of 30 minutes and the temperature of the reaction solution is allowed to come to 0° C. 300 µl of concentrated hydrochloric acid are subsequently added and the solution is stirred for 10 minutes at 0° C.

(d) Isolation:

The organic solvent is distilled off and the residue is adjusted to pH 7.5 using 10% ammonia solution with ice cooling. 20 ml of ethyl acetate and 10 ml of 10% strength sodium hydrogen carbonate solution are added and the mixture is stirred for 5 minutes. The ethyl acetate phase is separated off and washed once with 5 ml of saturated $NaHCO_3$ solution and twice with 10 ml of water. The ethyl acetate phase is then dried over sodium sulphate, filtered off from drying agents and chromatographed on silica gel (40 g, 0.04–0.063 mm) using the eluting agent ethyl acetate/n-hexane=1:5. The hard foam remaining after combining the fractions and stripping off the solvent is dissolved in 4 ml of dichloromethane, the solution is cooled to 0° C. and a mixture of 4 ml of trifluoroacetic acid and 0.3 ml of anisole is added. The solution is then stirred for 20 minutes at 0° C. to room temperature and subsequently concentrated to give an oil, the oil is dissolved in water and the solution is washed with ether. The aqueous phase is pumped onto an RP column (Hibar 250-25, Merck). The column is eluted, first with water, then with 1% to 10% strength methanol. The fractions are examined by means of analytical HPLC and the fractions which contain the (6R, 7S)-diastereomers are combined, methanol is distilled off in vacuo and the aqueous solution is lyophilized. 52 mg are obtained as a colorless lyophilisate.

C₁₇H₁₆ClN₅O₄S×2H₂O (457,89)

NMR (DCOOD): δ=1,5–1,67 (m, 1H); 1,86–1,96 (m, 1H); 2,6–2,8 (m, 2H); 4,05–4,15 (mm, 1H); 5,55 (d, 1H, J=4,9 Hz); 5,68 (s, 1H); 7,79–7,86 (q, 2H); 8,13 (s, 1H) ppm.

HPLC-analysis: Hibar 250-4, RP-8, 10 μm, 254 nm
Running agent: acetonitrile/acetic acid/water(100/30/870)
Flow: 3 ml min⁻¹/concentration: 1,0°/..

EXAMPLE 2

(+)-cis-(D)-7-[(2-Aminobenzothiazol-6-yl)-glycylamido]-1-azabicyclo[4,2,0]oct-2-en-8-one-2-carboxylic acid

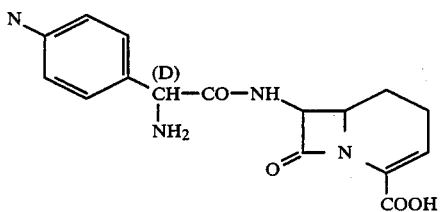

(a) Activation of the precursor acid:

547 mg [corresponds to 567 mg (1.57 mmol) of pure material; 1.3 equivalent] of sodium D-α-[(1-methyl-2-methoxycarbonylvinyl)-amino]-(2-aminobenzothiazol-6-yl)-acetate (purity=95%) are activated with 0.151 ml (1.57 mmol) of ethyl chloroformate for 30 minutes at −60° C. analogously to Example 1a.

(b) Preparation of the carbacephem component:

0.220 mg (1.21 mmol) of (±)-cis-7-amino-1-azabicyclo-[4,2,0]oct-2-en-8-one-2-carboxylic acid [EP No. 0,014,476, Kyowa Hakko Kogyo Co. 1980] are suspended in 4 ml of dimethylformamide and 0.8 ml of acetonitrile and converted into a clear solution by adding a few drops of 1N sodium hydroxide solution up to pH 8.1 with ice cooling.

(c) Coupling, deblocking and isolation of the betaine

The cooled carbacephem solution (0° C.) according to (b) is slowly added dropwise to the solution of the mixed anhydride and precursor acid according to (a) at −70° C. and the mixture is stirred for 10 minutes at −70° C. The temperature of the solution is subsequently allowed to come to 0° C. in the course of 45 minutes and the mixture is stirred with 1.0 mg of kieselguhr for a further 10 minutes. The reaction mixture is then filtered with suction through a Seitz filter, the filter is washed with dimethylformamide and 300 μl of 12N hydrochloric acid are added to the filtrate. The volume of the solution is highly concentrated and the filtrate is adjusted to pH 4.0 using 10% strength ammonia solution. The filtrate is pumped onto an RP-18 column (Hibar 250-25, Merck). The column is first eluted with water and then with water to which acetone is added from 2% to 10%. 30 fractions each having a volume of 10 ml are collected. Acetone is distilled off from the fractions which contain the desired diastereomer in pure form and the product is lyophilized.

EXAMPLE 3

(+)-c s-(D)-7-[(2-Aminobenzothiazol-6-yl)-glycylamido]-4-α-hydroxy-1-azabicyclo[4,2,0]oct-2-en-8-one-2-carboxylic acid

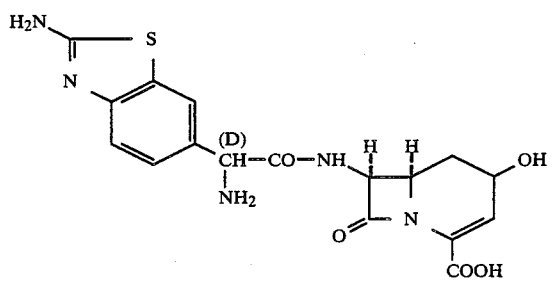

58.3 mg [corresponds to 55.4 mg (0.153 mmol) of pure material; 1.3 equivalents] of sodium D-α-[1-methyl-2-methoxycarbonylvinyl)-amino]-(2-aminobenzothiazol-6-yl)-acetate (purity=95%) are reacted with 30 mg (0.117 mmol) of t-butyl (±)-cis-78-amino-4-α-hydroxy-1-azabicyclo[4,2,0]oct-2-en-8-one-2-carboxylate (EP Pat. No. 0,025,602, Kyowa Hakko Kogyo Co. 1980) using 14.7 μl of ethyl chloroformate in dimethylformamide and acetonitrile in the presence of catalytic amounts of 3-dimethylamino-1-propanol analogously to Example 1a.

The t-butyl ester of the carbacephem derivative is treated with trifluoroacetic acid/methylene chloride (1:1) analogously to Example 1d. The trifluoroacetate isolated is dissolved in water and chromatographed on adsorber resin LPG 4429 (Lewatit ® OC 1062), first using water and subsequently using aqueous acetone with an increasing content of 1% to 10% of acetone.

EXAMPLE 4

(6R, 7S)-(D)-7-[(2-Amino-1H-benzimidazol-5-yl)glycylamido]-3-chloro-1-azabicyclo[4,2,0]oct-2-en-8-one-2-carboxylic acid

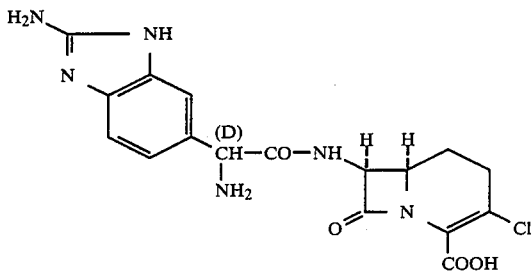

(a) Coupling reaction:

A mixture of 1.0 g (2.61 mmol) of benzhydryl (+)-cis-7-amino-3-chloro-1-azabicyclo[4,2,0]oct-2-en-8-one-2-carboxylate, 1.27 9 (3.13 mmol), 1.2 equivalents) of DL-α-t-butyloxycarbonylamino-α-(2-t-butyloxycarbonyl-1H-benzimidazol-5-yl)-acetic acid and 0.646 g (3.13 mmol, 1.2 equivalents) of dicyclohexylcarbodiimide (DCC) are stirred for 2.5 hours at room temperature in 30 ml of tetrahydrofuran. The solution is filtered off from deposited dicyclohexylurea, the deposit is washed with tetrahydrofuran and the solution is concentrated to dryness. The residue is taken up in ethyl acetate and successively washed once with saturated sodium hydrogen carbonate solution, once with sodium chloride solution, once with 10% strength hydrochloric acid and finally again with sodium chloride solution. The ethyl acetate phase is dried over sodium sulphate, filtered and the ethyl acetate is concentrated to dryness in vacuo.

(b) Deblocking and separation of diastereomers

The hard foam is dissolved in 5 ml of methylene chloride, the solution is cooled to 0° C. and 0.5 ml of anisole and 5 ml of trifluoroacetic acid are added successively. The mixture is subsequently stirred in a cold bath for 45 minutes the solution is concentrated to dryness and ether is added to the oily residue, during which the trifluoroacetate salt crystallizes out. The trifluoroacetate salt is dried in vacuo, subsequently dissolved in 25 ml of water and filtered through a membrane filter (Millipore, 45 μm). The filtrate is pumped onto an RP-18 column (Hibar 250-25, Merck). The column is continuously eluted, first with 200 ml of water, then with water to which an increasing content of methanol of 1 to 15% is continuously added. The fractions are examined using analytical HPLC and the eluates which contain the desired (6R, 7S)-(D)-diastereomers are combined. Methanol is distilled off in vacuo and the aqueous solution is lyophilized

EXAMPLE 5

(6R, 7S)-(D)-7-[(2-Aminobenzoxazol-5-yl)glycyl-amido]-3-chloro-1-azabicyclo[4,2,0]oct-2-en-8-one-2-carboxylic acid

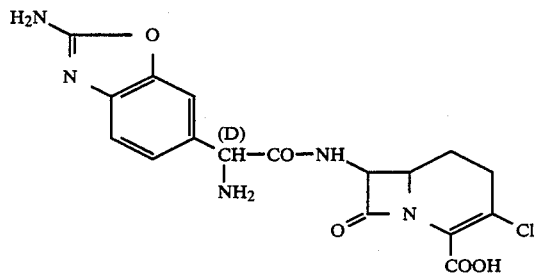

A mixture of 0.8 g (2.1 mmol) of benzhydryl (±)-cis-7-amino-3-chloro-1-azabicyclo[4,2,0]-oct-2-en-8-one-2-carboxylate, 0.82 g(2.52 mmol, 1.2 equivalents) of D-α-butylocycarbonylamino-α-(2-amino-benzoxazol-5-yl)-acetic acid monohydrate and 0.52 g(2.52 mmol 1.2 equivalents) of DCC are reacted analogously to Example 4. The Boc-protected carbacephem benzhydryl ester is deblocked using trifluoroacetic acid in methylene chloride analogously to Example 4 and the trifluoroacetate is chromatographed on an RP-18 column.

EXAMPLE 6

(6R, 7S)-(D)-7-[(Benzofuryl-5-yl)glycyl-amido]-3-chloro-1-azabicyclo[4,2,0]oct-2-en-8-one-2-carboxylic acid

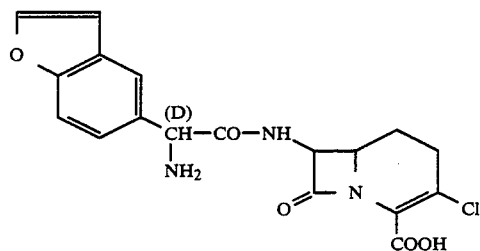

A mixture of 0.650 g (1.7 mmol) of benzhydryl (±)-cis-7-amino-1-azabicyclo[4,2,0]oct-2-en-8-one-2-carboxylate, 0.594 g (2.04 mmol, 1.2 equivalents) of DL-α-(t-butyloxycarbonylamino-α-benzofur-5-yl)a- cetic acid and 0.421 g(2.04 mmol, 1.2 equivalents) of DCC are reacted in tetrahydrofuran analogously to Example 4. The Boc-protected carbacephem benzhydryl ester is converted into the trifluoroacetate using trifluoroacetic acid in methylene chloride analogously to Example 4. The trifluoroacetate is dissolved in water with the addition of acetic acid, and the solution is pumped onto an RP-18 column (Hibar 250-25, Merck) and eluted with 3% acetic acid, to which methanol with an increasing content of 2% to 20% is added. The eluate, which contains the desired substance, is freeze-dried after distilling off methanol.

It will be understood that the specification and examples are illustrative but not limitative of the present invention and that other embodiments within the spirit and scope of the invention will suggest themselves to those skilled in the art.

We claim:

1. A heteroanellated phenylglycine-β-lactam antibiotic of the formula

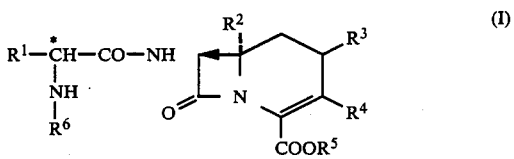

in which
R¹—stands for a radical of the formula

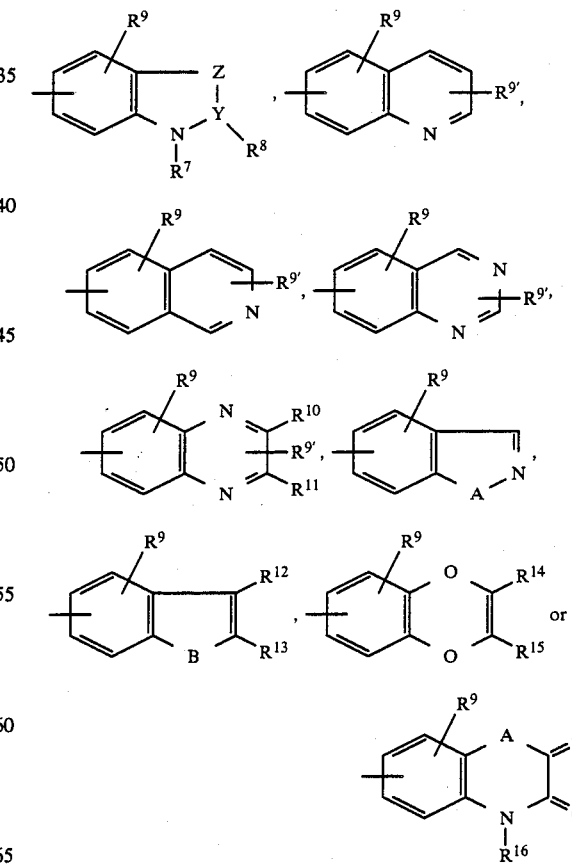

wherein
Y—stands for N or CR¹⁷, or the grouping

Y-R⁸—stands for $$\text{>=O or >=N-R}^8,$$

Z—stands for O, S or —NR¹⁸,
A—stands for O, S or —NR¹⁹,
B—stands for O or —NR¹⁶,
R⁷—stands for hydrogen or
stands for hydroxyl or amino, or
stands for straight-chain or branched alkyl or alkenyl, cycloalkyl or cycloalkenyl having up to 10 carbon atoms each of which is optionally substituted by halogen, optionally substituted amino, hydroxyl, cyano or optionally substituted phenyl, or
stands for optionally substituted phenyl,
R⁸—stands for hydrogen, or
stands for optionally substituted phenyl, or
stands for straight-chain or branched alkyl or alkenyl, cycloalkyl or cycloalkenyl having up to 10 carbon atoms, each of which is optionally substituted by halogen, hydroxyl, alkoxy or alkoxycarbonyl each having up to 6 carbon atoms cyano, carboxyl, optionally substituted amino group, or
R⁷ and R⁸ together complete a double bond
R⁹ and R⁹′ are identical or different and
stand for hydrogen, or
stand for straight-chain or branched alkyl alkoxy or alkylthio, cycloalkyl, cycloalkoxy or cycloalkylthio each having up to 8 carbon atoms, or
stand for trifluoromethyl or trifluoromethoxy, or
stand for hydroxyl, mercapto, nitro, cyano or halogen, or
stand for an optionally substituted amino group,
R¹⁰ and R¹¹ are identical or different and
stand for hydrogen, or
stand for optionally substituted phenyl, or
stand for an optionally substituted amino group, or
stand for hydroxyl, or
stand for a straight-chain or branched alkoxy or cycloalkoxy each having up to 8 carbon atoms, or
stand for acyl or acyloxy each having up to 7 carbon atoms, or
stand for straight-chain or branched optionally substituted alkyl or cyclolkyl having up to 12 carbon atoms,
R¹² and R¹³ are identical or different and
stand for hydrogen, or
stand for optionally substituted phenyl or
stand for heterocycyl, or
for hydroxyl, or
for an optionally substituted amino group or
for straight-chain or branched alkoxy or cycloalkoxy each having up to 8 carbon atoms, or
stand for acyl or acyloxy each having up to 7 carbon atoms, or
stand for alkoxycarbonyl having up to 8 carbon atoms, or
stand for optionally substituted straight-chain or branched alkyl or cycloalkyl each having up to 12 carbon atoms, or
R¹² and R¹³ together stand for the grouping of the formula

R¹⁴ and R¹⁵ are identical or different and
stand for hydrogen, or
stand for optionally substituted straight-chain chain branched alkyl or cycloalkyl each having up to 12 carbon atoms, or
stand for optionally substituted phenyl or
stand for alkoxycarbonyl having up to 8 carbon atoms,
R¹⁶ stands for hydrogen, or
for optionally substituted phenyl, or
stands for straight-chain or branched alkyl or cycloalkyl each having up to 8 carbon atoms,
R¹⁷ has the same meaning as R⁸ and in addition may stand for halogen,
for straight-chain or branched alkoxy or alkylthio, cycloalkoxy or cycloalkylthio each having up to 8 carbon atoms,
stand for an optionally substituted amino group,
stand for straight-chain or branched alkylsulphonyl or cycloalkylsulphonyl each having up to 8 carbon atoms,
stand for phosphono, sulpho or sulphamoyl,
stand for mercapto, hydroxyl, phenylthio or phenoxy,
stand for guanidino, amidino, hydrazino or hydroxylamino,
stand for optionally substituted heterocyclyl, or
stand for optionally substituted hetercyclyloxy or heterocyclylthio,
R¹⁸ has the same meaning as R¹⁷, but does not complete a double bond with R⁷, or
R¹⁷ and R¹⁸ together stand for a C₂-C₄-alkylene chain which is optionally interrupted within the alkylene chain by oxygen or sulphur and
R¹⁹ has the same meaning as R¹⁵ and can be identical to or different therefrom,
R²—stands for hydrogen or methoxy, or
for formamido, or
for hydroxylamino,
R³ stands for hydrogen, hydroxyl alkyl or alkoxy having up to 6 carbon atoms,
R⁴—denotes hydrogen, halogen, alkyl, alkoxy or alkylthio each having up to 4 carbon atoms trifluoromethyl, methoxymethyl, vinyl, carbamoyloxymethyl or acetyloxymethyl or
—stands for a group of the formula —CH=CH—CH₃, —CH=CH—C₂H₅, —CH=CH—CH₂Cl,

—CH=CH—CF₃, —CH=CH—CH₂OCH₃,

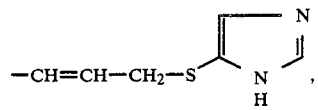

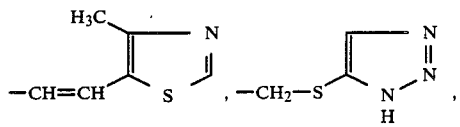

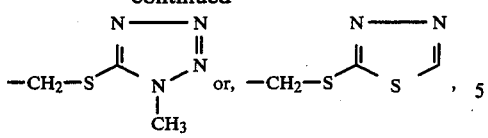

$R^5$—stands for hydrogen, or
for a carboxyl-protecting group, and
$R^6$—stands for hydrogen or for an amino protecting or a pharmaceutically tolerable salt thereof wherein
the term "optionally substituted amino" refers to the group

where
$R^{20}$ and $R^{21}$ are identical or different and
stand for hydrogen,
for phenyl,
for $C_1$-$C_8$-alkyl, for $C_7$-$C_{14}$ aralkyl; or
for $C_2$-$C_{10}$-acyl;
the term "optionally substituted phenyl" refers to substituted phenyl or phenyl which is unsubstituted or monosubstituted to tetrasubstituted by substituents independently selected from the group consisting of halogen straight-chain or branched alkyl, alkoxy, alkylthio or alkylsulphonyl, cycloalkyl, cycloalkoxy, cycloalkylthio or cycloalkylsulphonyl each having up to 10 carbon atoms, halogenoalkyl, halogenoalkoxy, or halogenoalkylthio each having up to 7 carbon atoms and up to 5 halogen atoms independently selected from the group consisting of chlorine and fluorine, or nitro, cyano, benzyl, sulpho amidino sulphamoyl, or carbamoyl;
the term "optionally substituted alkyl" refers to unsubstituted alkly or alkyl substituted by a substituent selected from the group consisting of halogen alkoxy or alkythio each having up to 8 carbon atoms, halogenoalkylthio alkylthio or halogenoalkoxy each having up to 8 carbon atoms and up to 5, halogen atoms independently selected from the group consisting of fluorine and chlorine atoms, nitro, cyano, an optionally substituted amino group, optionally substituted phenyl sulpho, sulphamoyl alkylsulphonyl having up to 6 carbon atoms, hydroxylmercapto acyloxy or acylthio each having up to 7 carbon atoms, carbamoyloxy carboxyl, alkoxycarbonyl having up to 8 carbon atoms phenoxy, phenylthio, benzyloxy or benzylthio;
the term "heterocyclyl" whether alone or as part of "heterocyclyloxy" or "heterocyclylthio" refers to a saturated or unsaturated heterocycle selected from the group consisting of pyrrolyl, pyrrolidinyl, pyrazolyl imidazolyl, pyridyl, pyridazinyl, pyrimidyl, pyrazinyl, quinolyl, isoquinolyl, indolyl, quinoxalyl, quinazolyl piperidinyl, morpholinyl, piperazinyl, thiopholinyl, furyl, thienyl oxazolyl, thiazolyl, isoxazolyl, thiadiazolyl trizolyl or tetrazolyl; and
the terms "optionally substituted heterocyclyl", "optionally substituted heterocyclyloxy", and "optionally substituted heterocyclthio" refer to "heterocyclyl", "heterocyclyloxy", and "heterocyclylthio" groups which are unsubstituted or monosubstituted, disubstituted or trisubstituted by substituents independently selected from the group consisting of straight-chain or branched alkyl, alkylthio or alkoxy each having up to 4 carbon atoms, halogen, nitro, cyano, hydroxyl, amino, trifluoromethyl, trifluoromethoxy or trifluoromethylthio.

2. A heteroanellated phenylglycin-$\beta$-Lactam antibiotic or salt thereof according to claim 1, in which
$R^1$ stands for a group of the formula

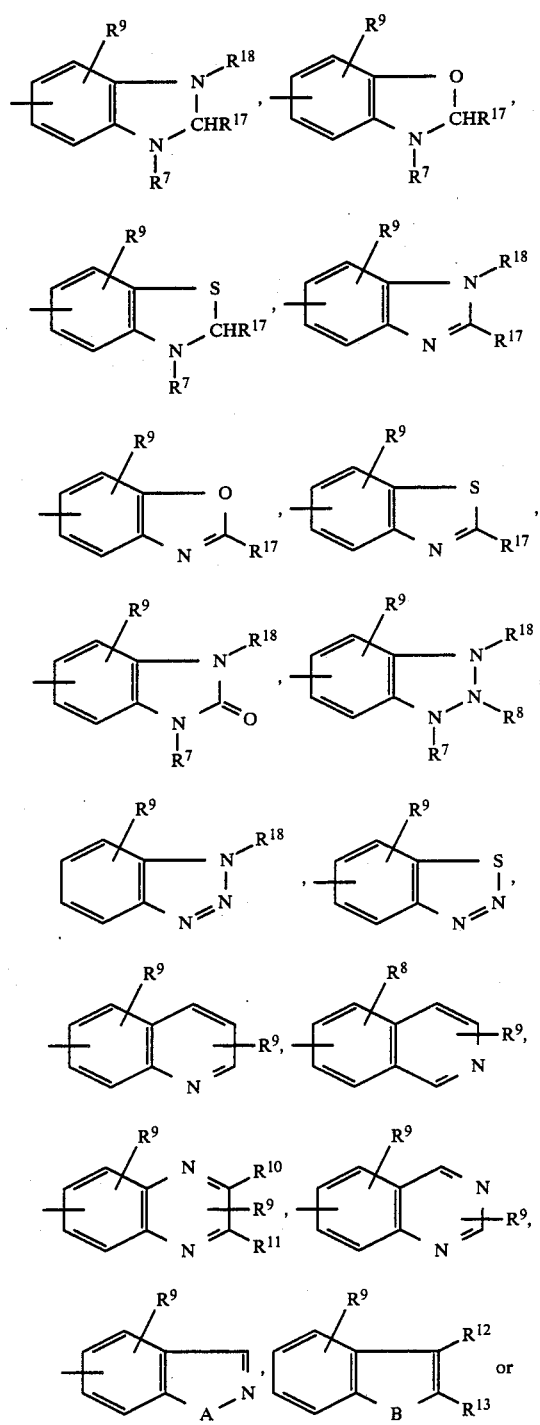

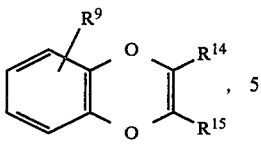

wherein
$R^7$ - stands for hydrogen, or
stands for hydroxyl or amino, or stands for straight-chain or branched alkyl or alkenyl, cycloalkyl or cycloalkenyl each having up to 8 carbon atoms, each of which is optionally substituted by one or more fluorine, chlorine, bromine, optionally substituted amino, hydroxyl or phenyl, or
stands for optionally substituted phenyl, $R^8$ stands for hydrogen, or
stands for optionally substituted phenyl, or
stands for straight-chain or branched alkyl or alkenyl, cycloalkyl or cycloalkenyl each having up to 8 carbon atoms, each of which is optionally substituted by one or more fluorine, chlorine, bromine, alkoxy having up to 4 carbon atoms, hydroxyl, carboxyl, phenyl, sulpho or an optionally substituted amino group, $R^9$ and $R^{9'}$ identical or different and
stand for hydrogen, or
stand for straight-chain or branched alkyl, alkoxy or alkylthio each having up to 6 carbon atoms, or
stand for trifluoromethyl or trifluoromethoxy, or
stand for hydroxyl, mercapto, nitro, cyano, fluorine, chlorine or bromine, or
stand for an optionally substituted amino group, $R^{10}$ and $R^{11}$ are identical or different and stand for hydrogen, or
stand for phenyl which is optionally monosubstituted or disubstituted by identical or different fluorine, chlorine, bromine, alkyl, alkoxy or alkylthio each having up to 4 carbon atoms, halogenoalkyl, halogenoalkoxy or halogenoalkylthio each having up to 3 carbon atoms and having one to three fluorine, by nitro, cyano, amino or dimethylamino, or
stand for an optionally substituted amino group, or
stand for hydroxyl or alkoxy having up to 6 carbon atoms, or
stand for benzyloxy or alkanoyloxy having up to 4 carbon atoms, or stand for straight-chain or branched alkyl or cycloalkyl having up to 8 carbon atoms, which is optionally substituted by one or more fluorine, chlorine, bromine, alkoxy or alkylthio each having up to 4 carbon atoms, halogenoalkoxy or halogenoalkylthio each having up to 4 carbon atoms and one to three fluorine, nitro, cyano, an optionally substituted amino group, phenyl, sulpho sulphamoyl, alkylsulphonyl having up to 2 carbon atoms, hydoxyl, mercapto, benzyloxy, alkanoyloxy having up to 4 carbon atoms, carbamoyloxy or alkoxycarbonyl having up to 4 carbon atoms, $R^{12}$ and $R^{13}$ are identical or different and
stand for hydrogen, or
stand for phenyl which is optionally monosubstituted or disubstituted by identical or different alkylthio each having up to 4 carbon atoms, halogenoalkyl, halogenoalkoxy, ahlogenoalkylthio each having up to 3 carbon atoms and having one to three fluorine, by nitro, cyano, dimethylamino or amino, or
stand for hydroxyl, or
stand for pyridyl, thienyl, furyl or pyrimidyl, or
stand for an optionally substituted amino group having the abovementioned meaning, or
stand for straight-chain or branched alkoxy or cycloalkoxy having up to 6 carbon atoms, or
stand for benzoyloxy or alkanoyloxy having up to 4 carbon atoms, or
stand for benzoyl or acetyl, or
stand for alkoxycarbonyl having up to 6 carbon atoms, or
stand for straight-chain or branched alkyl or cycloalkyl having up to 8 carbon atoms, which is optionally substituted by one to three fluorine, chlorine, bromine, alkoxy or alkylthio each having up to 4 carbon atoms, halogenoalkoxy or halogenoalkylthio each having up to 4 carbon atoms and having one to three fluorine, nitro, cyano, an optionally substituted amino group, phenyl, sulpho, sulphamoyl, alkylsulphonyl having up to 2 carbon atoms, hydroxyl, mercapto, banyloxy, alkanoyloxy having up to 4 carbon atoms, carbamoyloxy, alkoxycarbonyl having up to 4 carbon atoms, phenyloxy, phenylthio, benzyloxy or benzylthio, or $R^{12}$ and $R^{13}$ together stand for a grouping of the formula

$R^{14}$ and $R^{15}$ are identical or different and
stand for hydrogen, or
stand for straight-chain or branched alkyl or cycloalkyl having up to 8 carbon atoms, which is optionally substituted by one or more fluorine, chlorine, bromine, alkoxy or alkylthio each having up to 4 carbon atoms, halogenoalkoxy or halogenoalkylthio each having up to 4 carbon atoms and having one to three fluorine, nitro, cyano, an optionally substituted amino group, phenyl, sulpho, sulphamoyl, alkylsulphonyl having up to 2 carbon atoms, hydroxyl, mercapto, benzoyloxy, alkanoyloxy having up to 4 carbon atoms, carbamoyloxy or alkoxycarbonyl having up to 4 carbon atoms, or
stand for phenyl which is optionally monosubstituted or disubstituted by identical or different fluorine, chlorine, bromine, alkyl, alkoxy or alkylthio each having up to 4 carbon atoms, halogenoalkyl, halogenoalkoxy or halogenoalkylthio each having up to three carbon atoms and one to three fluorine, nitro, cyano, amino or dimethylamino, or
stand for alkoxycarbonyl having up to 6 carbon atoms,
stands for O, S or $-NR_{19}$,
B—stands for O or $-NR^{16}$,
$R^{16}$ stands for hydrogen, or
for phenyl, or
for straight-chain or branched alkyl or cycloalkyl having up to 6 carbon atoms,
$R^{17}$ has the same meaning as $R^8$ and in addition stands for fluorine, chlorine or bromine, or
stands for alkoxy, alkylthio or alkylsulphonyl each having up to 6 carbon atoms, or
stands for an optionally substituted amino group, or
stands for phosphono, sulpho, sulphamoyl, hydroxyl, mercapto, phenylthio or phenyloxy, or
stands for guanidino, hydrazino or hydroxylamino, stands for optionally substituted heterocyclyl, heterocyclyloxy or heterocyclylthio, $R^{18}$ has the same meaning as $R^{17}$, but does not complete a double bond with $R^7$, or $R^{17}$ and $R^{18}$ together stand for a $C_2$-$C_4$-alkylene chain which is optionally interrupted within the alkylene chain by sulphur, and $R^{19}$ has the same meaning as $R^{16}$ and can be identical to or different therefrom, $R^2$—stands for hydrogen, or
for methoxy, or
stands for formamido or hydroxylamino, $R^3$—stands for hydrogen, hydroxyl, alkyl or alkoxy having up to 4 carbon atoms, $R^4$—stands for hydrogen, chlorine, fluorine, methyl, ethyl, methoxy, methylthio, trifluoromethyl, methoxymethyl, vinyl, carbamoyloxymethyl or acetyloxymethyl, or
denotes a group of the formula —CH=CH—CH₃, —CH=CH—C₂H₅, —CH=CH—CH₂Cl,

—CH=CH—CF₃,

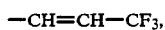

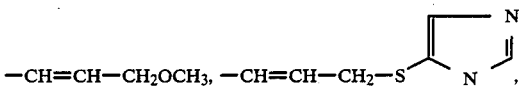

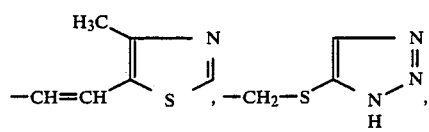

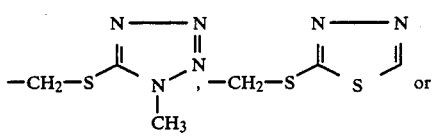

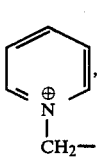

and
$R^5$—stands for hydrogen, or
stands for methyl, ethyl, tert.-butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-benzyl, 2-nitrobenzyl, trimethylsilylethyl or tert.-butyldimethylsilylethyl, or
stands for a radical of the formula

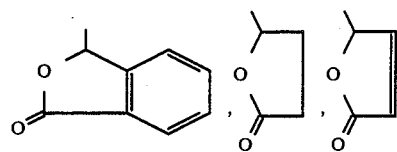

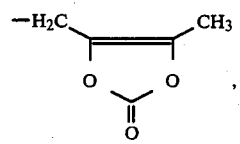

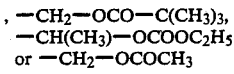

and
$R^6$ stands for hydrogen.

3. A heteroanellated phenylglycin-β-Lactam antibiotic according to claim 1, in which $R^1$—stands for a group of the formula

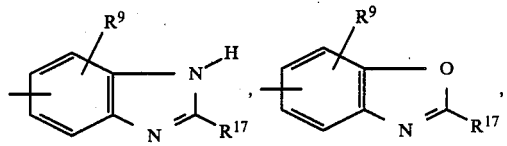

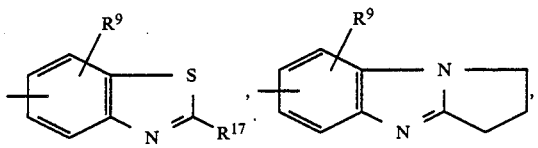

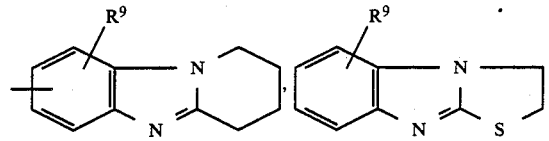

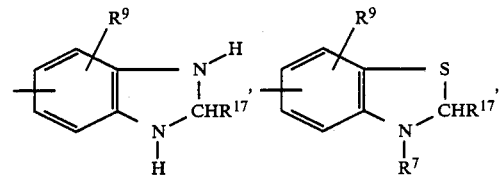

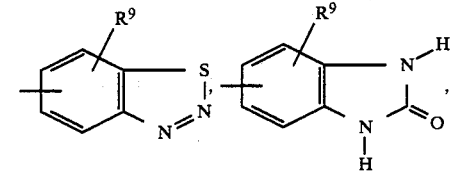

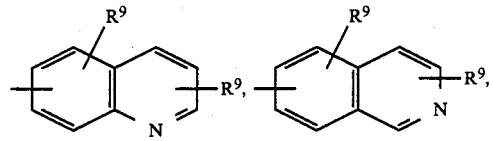

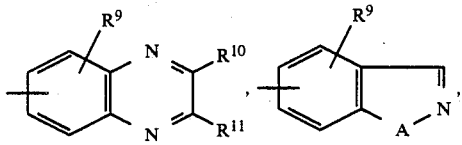

-continued

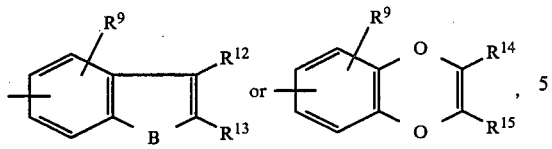

wherein
R⁷—stands for hydrogen, or
stands for straight-chain or branched alkyl or alkenyl, cycloalkyl or cycloalkenyl having up to 6 carbon atoms, each of which is optionally substituted by fluorine, amino, hydroxyl or phenyl, or
stands for optionally substituted phenyl,
R⁹ and R⁹′ are identical or different and
stand for hydrogen, or
stand for straight-chain or branched alkyl, alkoxy or alkylthio each having up to 4 carbon or
stand for trifluoromethyl or trifluoromethoxy, or
stand for hydroxyl, nitro, cyano, fluorine or chlorine, or
stand for amino, methylamino, dimethylamino, phenylamino or acetylamino,
R¹⁰ and R¹¹ are identical or different and stand for hydrogen, or
stand for phenyl which is optionally substituted by chlorine, fluorine, alkyl having up to 4 carbon atoms, methoxy, methylthio, trifluoromethyl, trifluoromethoxy, trifluoromethylthio, nitro, cyano, amino or dimethylamino, or
stand for amino, methylamino, dimethylamino, phenylamino or acetylamino, or
stand for hydroxyl, or
stand for alkoxy having up to 4 carbon atoms, or
stand for benzoyloxy or acetyloxy, or
stand for straight-chain or branched alkyl or alkenyl, cycloalkyl or cycloalkenyl each having up to 6 carbon atoms, each of which can be substituted by fluorine, chlorine, methoxy, methylthio, trifluoromethoxy or cyano,
R¹² and R¹³ are identical or different and
stand for hydrogen, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for pyridyl, thienyl, furyl, pyridyl or hydroxyl, or
stand for amino, methylamino, dimethylamino, phenylamino or acetylamino, or
stand for alkoxy having up to 4 carbon atoms, or
stand for benzoyloxy or acetyloxy, or
stand for benzoyl or acetyl, or
stand for alkoxycarbonyl having up to 4 carbon atoms, or
stand for straight-chain or branched or alkenyl, cycloalkyl or cyclic alkenyl having up to 6 carbon atoms, each of which is optionally substituted by fluorine, chlorine, methoxy, methylthio, trifluoromethoxy, cyano, phenyloxy or benzyloxy,
R¹⁴ and R¹⁵ are identical or different and
stand for hydrogen, or
stand for straight-chain or branched alkyl or alkenyl, cycloalkyl or cycloalkenyl having up to 6 carbon atoms, each of which optionally substituted by fluorine, chlorine, methoxy, methylthio, trifluoromethoxy or cyano, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or stand for alkoxycarbonyl having up to 4 carbon atoms,
A—stands for O, S or —NR¹⁹,
B—stands for O or —NR¹⁶,
R¹⁶ stands for hydrogen, or
stands for phenyl, or
stands for straight-chain or branched alkyl having up to 4 carbon atoms,
R¹⁷ stands for hydrogen, or
stands for straight-chain or branched alkyl or alkenyl each having up to 4 carbon atoms, each of which is optionally substituted by fluorine, chlorine, alkoxy having up to 4 carbon atoms, hydroxyl, carboxyl, phenyl, sulpho, amino, alkylamino or dialkylamino each having up to 3 carbon atoms per alkyl group, phenylamino, benzylamino or by acetylamino, or
stands for fluorine, chlorine or bromine, or
stands for alkoxy or alkylthio each having up to 4 carbon atoms, or
stands for phenyl, or
stands for amino, alkylamino or dialkylamino each having up to 3 carbon atoms per alkyl group, phenylamino, benzylamino or acetylamino, or
stands for alkylsulphonyl having up to 4 carbon atoms, or
stands for sulpho or sulphamoyl, or
stands for hydroxyl, mercapto, phenyloxy or phenylthio, or
stands for guanidino, hydrazino or hydroxylamino, or
stands for pyrrolyl, pyrrolidinyl, pyrazolyl, imidazolyl, pyridyl, quinolyl, isoquinolyl, furyl, thienyl, morpholinyl, piperidinyl, piperazinyl or pyrimidyl, each of which can be substituted by fluorine, chlorine, methyl, nitro, cyano, hydroxyl, trifluoromethyl, methoxy or amino, or
stands for pyridylthio or pyridyloxy,
R¹⁸—has the same meaning as R¹⁷ and can be identical to or different therefrom, and
R¹⁹—has the same meaning as R¹⁶ and is identical to or different therefrom,
R²—stands for hydrogen, or
stands for methoxy, or
stands for formamido or hydroxylamino,
R³—stands for hydrogen, hydroxyl, methyl or methoxy,
R⁴—stands for hydrogen, chlorine, methyl, methoxy, methoxymethyl, vinyl, cis-propenyl or acetyloxymethyl, or
R⁵—stands for hydrogen, or
stands for a radical of the formula —CH₂—OCOCH₃,

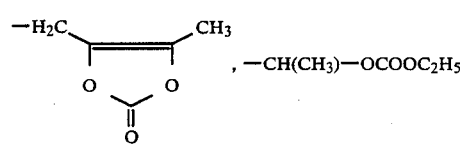
, —CH(CH₃)—OCOOC₂H₅

-continued or —CH$_2$—OCO—C(CH$_3$)$_3$ and

R$^6$—stands for hydrogen, or its sodium salt.

4. A compound according to claim 1, wherein such compound is (6S, 7S)-(D)-[(2-aminobenzothiazol-6-yl)glycyl-amido]-3-chloro-1-azabicyclo[4,2,0]oct-2-en-8-one-2-carboxylic acid of the formula

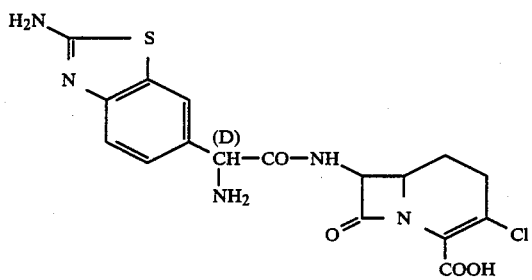

or a pharmaceutically tolerable salt thereof.

5. A compound according to claim 1, wherein such compound is (+)-cis-(D)-7-[(2-aminobenzothiazol-6-yl)-glycyl-amido]-1-azabicyclo[4,2,0]oct-2-en-8-one-2-carboxylic acid of the formula

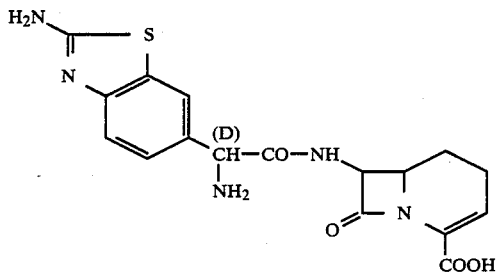

or a pharmaceutically tolerable salt thereof.

6. A compound according to claim 1, wherein such compound is (+)-cis-(D)-7-[(2-aminobenzothiazol-6-yl)-glycyl-amido]-4-α-hydroxy-1-azabicyclo[4,2,0]oct-2-en-8-one-2-carboxylic acid of the formula

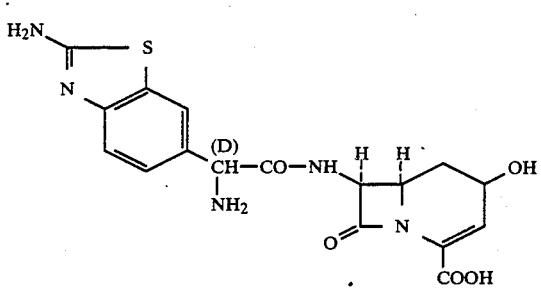

or a pharmaceutically tolerable salt thereof.

7. A compound according to claim 1, wherein such compound is (6R, 7S)-(D)-7-[(2-amino-1H-benzimidazol-5-yl)glycyl-amido]-3-chloro-1-azabicyclo[4,2,0]oct-2-en-8-one-2-carboxylic acid of the formula

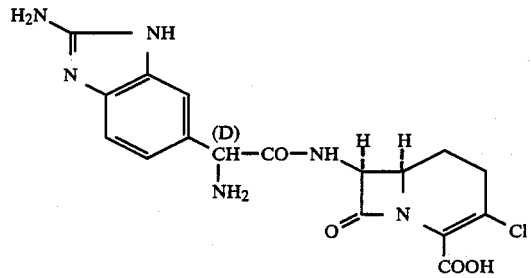

or a pharmaceutically tolerable salt thereof.

8. A compound according to claim 1, wherein such compound is (6R, 7S)-(D)-7-[(2-aminobenzoxazol-5-yl)glycyl-amido]-3-chloro-1-azabicyclo[4,2,0]oct-2-en-8-one-2-carboxylic acid of the formula

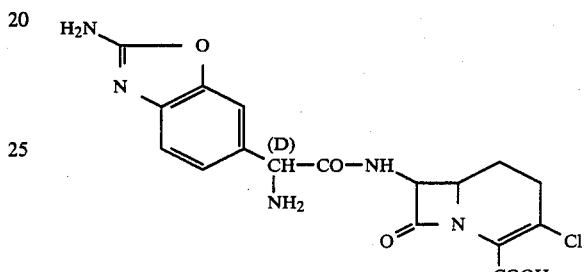

or a pharmaceutically tolerable salt thereof.

9. A compound according to claim 1, wherein such compound is (6R, 7S)-(D)-7-[(benzofuryl-5-yl)glycyl-amido]-3-chloro-1-azabicyclo[4,2,0]oct-2-en-8-one-2-carboxylic acid of the formula

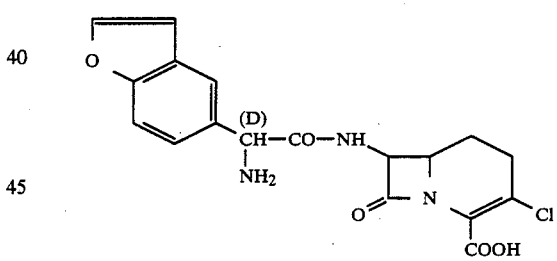

or a pharmaceutically tolerable salt thereof.

10. An antibacterial composition comprising an antibacterially effective amount of a compound or salt according to claim 1 and a pharmaceutically acceptable diluent.

11. A composition according to claim 10 in the form of a tablet, capsule or ampule.

12. A method of combating bacteria in a patient which comprises administering to such patient an antibacterially effective amount of a compound or salt according to claim 1.

13. The method according to claim 12, wherein such compound is (6S, 7S)-(D)-[(2-aminobenzothiazol-6-yl)glycyl-amido]-3-chloro-1-azabicyclo[4,2 0)oct-2-en-8-one-2-carboxylic acid, (+)-cis-(D)-7-[(2-aminobenzothiazol-6-yl)-glycyl-amido]-1-azabicyclo[4,2,0]oct-2-en-8-one-2-carboxylic acid, (+)-cis-(D)-7-[(2-aminobenzothiazol-6-yl)-glycyl-amido]-4-α-hydroxy-1-azabicyclo[4,2,0]oct-2-en-8-one-2-carboxylic acid
(6R, 7S)-(D)-7-[(2-amino-1H-benzimidazol-5-yl)glycylamido]-3-chloro-1-azabicyclo[4,2,0]oct-2-en-8-one-2-carboxylic acid,
(6R, 7S)-(D)-7-[(2-aminobenzoxazol-5-yl)glycyl-amido]-3-chloro-1-azabicyclo[4,2,0]oct-2-en-8-one-2-carboxylic acid, or
(6R, 7S)-(D)-7-[(benzofuryl-5-yl)glycyl-amido]-3-chloro-1-azabicyclo[4,2,0]oct-2-en-8-one-2-carboxylic acid, or a pharmaceutically tolerant salt thereof.

* * * * *